(12) United States Patent
Nagae et al.

(10) Patent No.: US 9,801,602 B2
(45) Date of Patent: Oct. 31, 2017

(54) X-RAY DIAGNOSTIC APPARATUS TO IDENTIFY A TARGET IN X-RAY IMAGES

(71) Applicant: Toshiba Medical Systems Corporation, Otawara-shi (JP)

(72) Inventors: Ryoichi Nagae, Nasushiobara (JP); Yasuto Hayatsu, Otawara (JP); Yoshiaki Iijima, Nasushiobara (JP); Kunio Shiraishi, Otawara (JP); Yoshinori Shimizu, Nasushiobara (JP); Yuichiro Watanabe, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 176 days.

(21) Appl. No.: 14/809,613

(22) Filed: Jul. 27, 2015

(65) Prior Publication Data

US 2016/0029989 A1    Feb. 4, 2016

(30) Foreign Application Priority Data

Aug. 1, 2014   (JP) ................. 2014-158093

(51) Int. Cl.
*A61B 6/12*      (2006.01)
*A61B 6/00*      (2006.01)
(Continued)

(52) U.S. Cl.
CPC .......... *A61B 6/5205* (2013.01); *A61B 6/0457* (2013.01); *A61B 6/0492* (2013.01);
(Continued)

(58) Field of Classification Search
CPC ....... A61B 6/0457; A61B 6/0492; A61B 6/06; A61B 6/12; A61B 6/4441; A61B 6/4482;
(Continued)

(56) References Cited

U.S. PATENT DOCUMENTS 7,415,169 B2   8/2008  Florent et al.
8,594,271 B2   11/2013 Sakaguchi et al.
(Continued)

FOREIGN PATENT DOCUMENTS

JP   2005-510288   4/2005
JP   2010-131371   6/2010
(Continued)

*Primary Examiner* — Siamak Harandi
(74) *Attorney, Agent, or Firm* — Oblon, McClelland, Maier & Neustadt, L.L.P.

(57) ABSTRACT

In an X-ray diagnostic apparatus of one embodiment, an image data generator sequentially generates X-ray images based on X-rays transmitted through a subject. An image processor executes: first processing where, in response to an instruction to start correction processing, a position of a target contained in a predetermined X-ray image is obtained as a reference position; and second processing where corrected images in which positions of the target are set at the reference position are sequentially generated from newly generated X-ray images. An image data storage unit stores therein information on a reference position with respect to each set of conditions of manipulation on the subject. Upon receiving the instruction to start correction processing, the image processor executes the second processing by using information on the reference position stored in the image data storage unit, in accordance with a set of the conditions of manipulation on the subject.

20 Claims, 25 Drawing Sheets

(51) Int. Cl.
*A61B 6/04* (2006.01)
*G06T 5/00* (2006.01)
*G06T 7/246* (2017.01)
*A61B 6/06* (2006.01)

(52) U.S. Cl.
CPC .............. *A61B 6/12* (2013.01); *A61B 6/4441* (2013.01); *A61B 6/4482* (2013.01); *A61B 6/463* (2013.01); *A61B 6/469* (2013.01); *A61B 6/487* (2013.01); *A61B 6/503* (2013.01); *A61B 6/504* (2013.01); *A61B 6/5217* (2013.01); *A61B 6/5223* (2013.01); *A61B 6/5264* (2013.01); *G06T 5/006* (2013.01); *G06T 7/248* (2017.01); *A61B 6/06* (2013.01); *A61B 6/488* (2013.01); *A61B 6/5288* (2013.01); *A61B 6/541* (2013.01); *A61B 6/542* (2013.01); *A61B 6/547* (2013.01); *A61B 6/588* (2013.01); *G06T 2207/10121* (2013.01); *G06T 2207/20081* (2013.01); *G06T 2207/20104* (2013.01); *G06T 2207/30052* (2013.01); *G06T 2207/30101* (2013.01)

(58) Field of Classification Search
CPC ......... A61B 6/463; A61B 6/469; A61B 6/487; A61B 6/488; A61B 6/503; A61B 6/504; A61B 6/5205; A61B 6/5217; A61B 6/5223; A61B 6/5264; A61B 6/5288; G06T 2207/10121; G06T 2207/20081; G06T 2207/20104; G06T 2207/30052; G06T 2207/30101; G06T 5/006; G06T 7/248

See application file for complete search history.

(56) References Cited

U.S. PATENT DOCUMENTS

| | | | |
|---|---|---|---|
| 2007/0010743 A1* | 1/2007 | Arai | A61B 8/13 600/443 |
| 2010/0104167 A1* | 4/2010 | Sakaguchi | A61B 6/12 382/132 |
| 2014/0051991 A1 | 2/2014 | Sakaguchi et al. | |

FOREIGN PATENT DOCUMENTS

| WO | WO 03/045263 A2 | 6/2003 |
|---|---|---|
| WO | WO 2012/143971 A1 | 10/2012 |

* cited by examiner

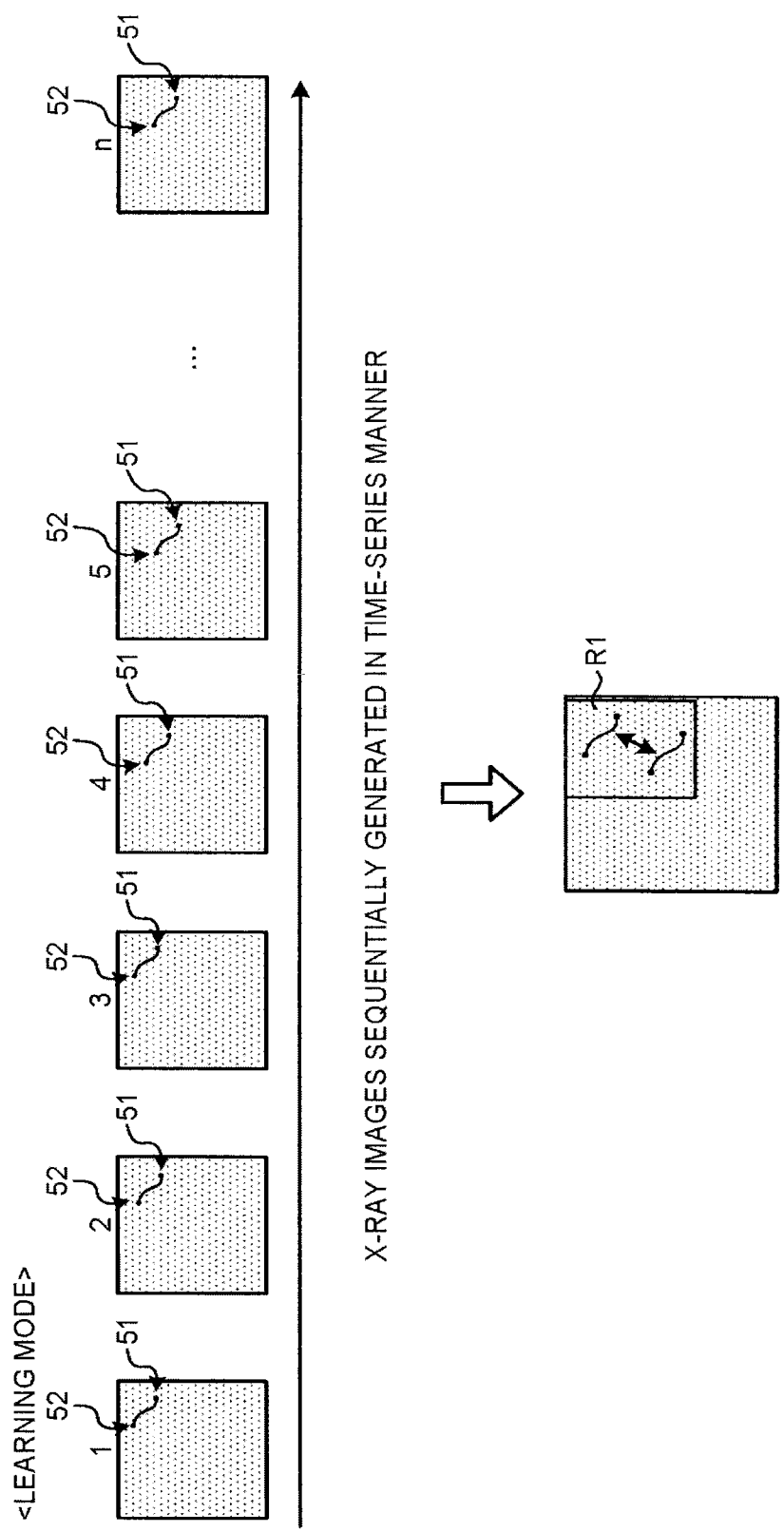

DISPLAY IMAGES FROM FIRST FRAME

DISPLAY IMAGES FROM FIRST FRAME

DESIGNATE MARKER IN PRELIMINARY IMAGE CORRESPONDING TO END-SYSTOLE

DESIGNATE MARKER IN PRELIMINARY IMAGE CORRESPONDING TO END-DIASTOLE

CORRECTION VECTORS   $\vec{C}_1$   $\vec{C}_2$   $\vec{C}_3$   ...   $\vec{C}_n$ PERIODIC TRACE DATA IN WHICH AVERAGE CORRECTION VECTOR IS ASSOCIATED WITH CARDIAC PHASE

REFERENCE POINT
(70% IN R-R INTERVAL)

M% IN R-R INTERVAL
AVERAGE CORRECTION VECTOR $\vec{C}_M$

NEW IMAGES TO BE SUBJECTED TO IMAGE PROCESSING

FIG.32

| CONTENT OF CONDITIONS | | | | | RESULT OF LEARNING MODE |
|---|---|---|---|---|---|
| ARM ANGLE | COUCH HEIGHT | FOV | SID | ... | |
| | | | | | |
| | | | | | |
| | | | | | |

X-RAY DIAGNOSTIC APPARATUS TO IDENTIFY A TARGET IN X-RAY IMAGES

CROSS-REFERENCE TO RELATED APPLICATIONS

This application is based upon and claims the benefit of priority from Japanese Patent Application No. 2014-158093, filed on Aug. 1, 2014; the entire contents of which are incorporated herein by reference.

FIELD

Embodiments described herein relate generally to an X-ray diagnostic apparatus.

BACKGROUND

Endovascular intervention treatment is treatment for treating an affected area in the heart, brain, liver, or other organs by inserting a treatment tool (device) called a catheter into a blood vessel. For example, in endovascular intervention treatment, a doctor inserts a balloon-tip catheter to a stricture site. The doctor then, for example, injects fluid into the balloon through the catheter and expands the balloon. The stricture site is thereby expanded to restore the blood flow. The stricture site is thereby mechanically expanded to restore the blood flow. The balloon-tip catheter is pulled out of the body by the doctor after the fluid in the balloon is sucked.

In order to prevent restenosis of the stricture site expanded by the balloon, endovascular intervention treatment is conducted using a balloon-tip catheter having a metal mesh (stent strut) affixed to the outside of the balloon. In this treatment, the doctor expands the stent strut by expanding the balloon and thereafter sucks the fluid in the balloon and pulls the catheter out of the body. The expanded stent strut is retained at the stricture site, thereby reducing the possibility of restenosis at the stricture site. The balloon-tip catheter having a stent strut is called a "stent".

In endovascular intervention treatment, it is necessary to move the device inserted into a blood vessel precisely to a treatment target site. In general, the device is positioned with reference to an X-ray image generated and displayed real-time by an X-ray diagnostic apparatus. For this purpose, the device has, for example, x-ray-opaque metal attached at two places (or one place in some cases) as markers indicating the position of the balloon or the stent. The doctor positions the device by referring to the markers visualized in the X-ray image appearing on a monitor.

However, when endovascular intervention treatment is conducted on a blood vessel in an organ such as the heart that always pulses or an organ that moves because of pulsation, the position of the device in the X-ray image always moves. It is therefore an extremely skillful task for doctors to position the device by referring to the X-ray image.

There is conventionally known a technique for displaying moving images in which the device appears virtually stationary, for example, by tracking the markers at two points visualized in the successively generated X-ray images and deforming the images such that the markers at two points in each X-ray image are located at the same positions as in the past images. A technique as a post-process is also known, which is for highlighting the device at a high contrast, for example, by obtaining the arithmetic mean of images of a plurality of frames in which the positions of the markers at two points are corrected to be the same position.

BRIEF DESCRIPTION OF DRAWINGS

FIG. 5 is a diagram for explaining one example of a Learning mode according to the first embodiment;

FIG. 32 is a diagram for explaining one example of information for the Learning mode.

DETAILED DESCRIPTION

According to an embodiment, an X-ray diagnostic apparatus includes processing circuitry and storage circuitry. The processing circuitry configured to sequentially generate X-ray images based on X-rays emitted from an X-ray tube and transmitted through a subject. The processing circuitry configured to execute first processing where, in response to an instruction to start correction processing, a position of a target contained in a predetermined X-ray image is obtained as a reference position, and second processing where corrected images in which positions of the target are set at the reference position are sequentially generated from newly generated X-ray images. The storage circuitry configured to store therein information on the reference position with respect to each set of conditions of manipulation on the subject. Upon receiving the instruction to start correction processing, the processing circuitry is configured to execute the second processing by using information on the reference position stored in the storage circuitry in accordance with a set of the conditions of manipulation on the subject.

The following describes embodiments of X-ray diagnostic apparatuses in detail with reference to the accompanying drawings.

First Embodiment

Figure 1:
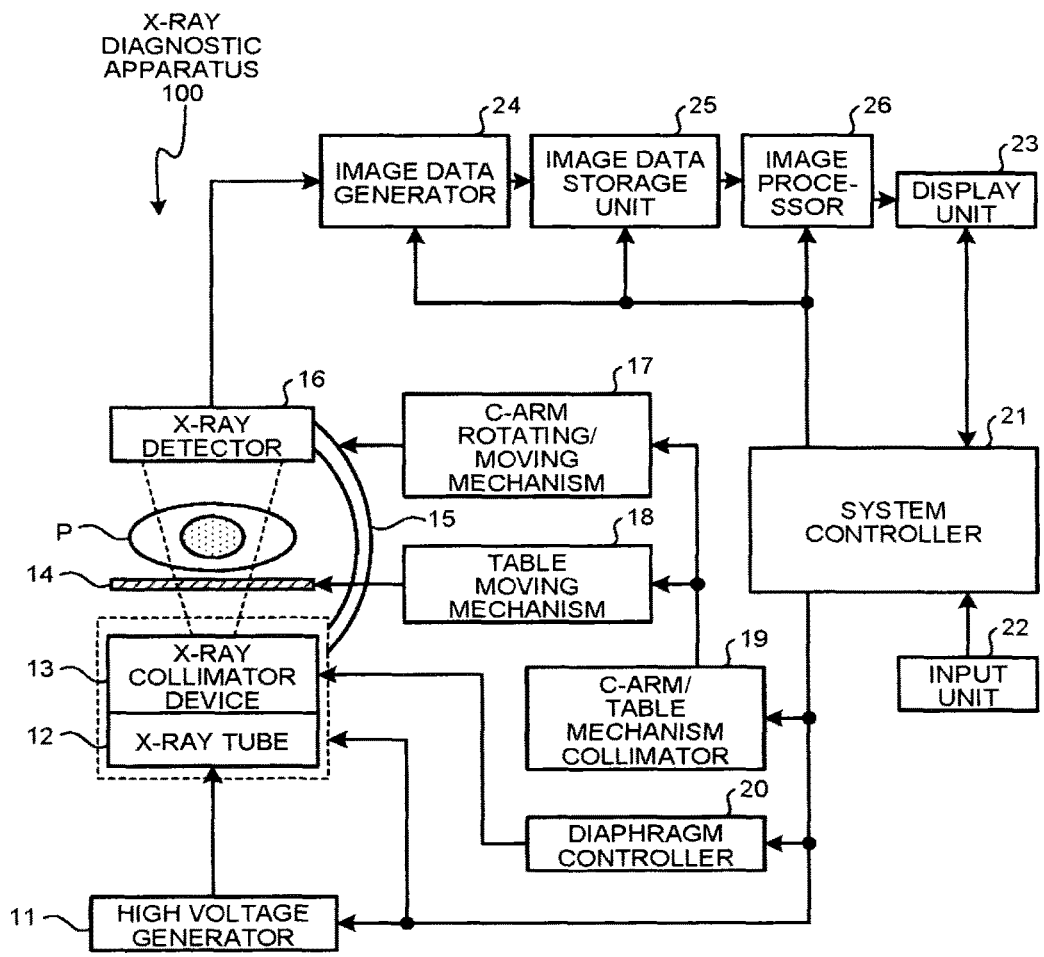
FIG. 1 is a diagram illustrating one example of the configuration of an X-ray diagnostic apparatus according to a first embodiment.

First, the overall configuration of an X-ray diagnostic apparatus according to a first embodiment is described. FIG. 1 is a diagram illustrating one example of the configuration of an X-ray diagnostic apparatus 100 according to the first embodiment. As illustrated in FIG. 1, the X-ray diagnostic apparatus 100 according to the first embodiment includes a high voltage generator 11, an X-ray tube 12, an X-ray collimator device 13, a table 14, a C-arm 15, an X-ray detector 16, a C-arm rotating/moving mechanism 17, a table moving mechanism 18, a C-arm/table mechanism controller 19, a collimator controller 20, a system controller 21, an input unit 22, a display unit 23, an image data generator 24, an image data storage unit 25, and an image processor 26.

Functions, described below, of the above described units are each constructed as a computer program, and implemented by a circuitry executing the computer program. For example, processing functions to be performed by the C-arm/table mechanism controller 19, the collimator controller 20, the system controller 21, the image data generator 24, and the image processor 26 are stored in computer-executable forms in the image data storage unit 25 (also referred to as an image data storage circuitry) or a storage circuitry that is not illustrated. Circuitry read out corresponding computer programs from the image data storage unit 25 or the storage circuitry (not illustrated), and executes the computer programs, thereby implementing functions corresponding to the respective programs.

Here, a single circuit or a plurality of circuits may be used as a circuit or circuits to execute each of the functions. More specifically, a single circuit may read out a computer program corresponding to each of the functions and implement a corresponding function, or alternatively, a plurality of circuits may read out computer programs corresponding to different functions and implement corresponding functions. Each of the above-described circuits is a processor that reads out a computer program from the image data storage unit 25 or the storage circuitry (not illustrated) and executes the computer program to implement a function corresponding to the computer program.

The term "processor" used in the above explanation refers to, for example, a circuit such as a central processing unit (CPU), a graphics processing unit (GPU), or an application specific integrated circuit (ASIC), a programmable logic device (for example, a simple programmable logic device (SPLD), a complex programmable logic device (CPLD), or a field programmable gate array (FPGA)). The processor reads out a computer program stored in a storage circuit and executes the computer program to implement a function. Storing a computer program in the storage circuit may be changed to embedding the computer program directly in a circuit of the processor. In this case, the processor reads the computer program embedded in the circuit and executes the computer program to implement the function. Each processor of this embodiment is not limited to a processor constructed of a single circuit, and may be constructed as a single processor having a plurality of independent circuits combined therein to implement an intended function.

The high voltage generator 11 is a device that generates high voltage and supplies the generated high voltage to the X-ray tube 12. The X-ray tube 12 is a device that generates X-rays using the high voltage supplied from the high voltage generator 11. The high voltage generator 11 adjusts the X-ray dose applied to a subject P and controls ON/OFF of X-ray irradiation on the subject P by adjusting the voltage supplied to the X-ray tube 12. The X-ray collimator device 13 is a device for narrowing X-rays generated by the X-ray tube 12 such that the X-rays are selectively applied to a region of interest of the subject P. For example, the X-ray collimator device 13 has four slidable collimator blades, and the collimator blades are slid to narrow X-rays generated by the X-ray tube 12 and apply the narrowed X-rays to the subject P.

The table 14 is a bed on which the subject P lies, and is disposed on a couch (not illustrated). The X-ray detector 16 detects X-rays transmitted through the subject P. For example, the X-ray detector 16 has detection elements arranged in a matrix. Each detection element converts X-rays transmitted through the subject P into an electrical signal, accumulates the thus converted electrical signals, and transmits the accumulated electrical signals to the image data generator 24 described later. The C-arm 15 is an arm for holding the X-ray tube 12, the X-ray collimator device 13, and the X-ray detector 16. "The X-ray tube 12 and the X-ray collimator device 13" and the X-ray detector 16 are disposed so as to be opposed to each other by the C-arm 15 with the subject P placed therebetween.

The C-arm rotating/moving mechanism 17 is a mechanism for rotating and moving the C-arm 15. The C-arm rotating/moving mechanism 17 can change a source image receptor distance (SID) that is the distance between the X-ray tube 12 and the X-ray detector 16. The C-arm rotating/moving mechanism 17 can also rotate the X-ray detector 16 held by the C-arm 15. The table moving mechanism 18 is a mechanism for moving the table 14. The C-arm/table mechanism controller 19 adjusts the rotation and movement of the C-arm 15 and the movement of the table 14 by controlling the C-arm rotating/moving mechanism 17 and the table moving mechanism 18 under the control of the system controller 21 described later. The C-arm/table mechanism controller 19 is also referred to as a C-arm/table mechanism control circuitry, and reads out a computer program corresponding to the above-described C-arm/table mechanism controlling function from the image data storage unit 25 or the storage circuitry (not illustrated), and executes the computer program. The collimator controller 20 controls an irradiation range of X-rays applied to the subject P by adjusting the aperture of the collimator blades of the X-ray collimator device 13 under the control of the system controller 21 described later. The collimator controller 20 is also referred to as a collimator control circuitry, and reads out a computer program corresponding to the above-described collimator controlling function from the image data storage unit 25 or the storage circuitry (not illustrated), and executes the computer program.

The image data generator 24 generates X-ray images based on X-rays emitted from the X-ray tube 12 and transmitted through the subject. Specifically, the image data generator 24 generates X-ray images by use of the electrical signals converted from X-rays by the X-ray detector 16 and tores the generated X-ray images into the image data storage unit 25. For example, the image data generator 24 performs current/voltage conversion, A (analog)/D (digital) conversion, and parallel/serial conversion on the electrical signals received from the X-ray detector 16 and generates image data. The image data generator 24 is also referred to as an image data generation circuitry, and reads out a computer program corresponding to the above-described image data generating function from the image data storage unit 25 or the storage circuitry (not illustrated), and executes the computer program.

The image data storage unit 25 stores therein X-ray images generated by the image data generator 24. The image data storage unit 25 is also referred to as an image data storage circuitry, and stores therein, for example, computer programs corresponding to the respective functions. The image processor 26 is a processor that executes a variety of image processing on X-ray images stored in the image data storage unit 25. This image processing is described later in detail. The image processor 26 executes a variety of image processing on X-ray images generated by the image data generator 24. For example, the image processor 26 acquires an X-ray image directly from the image data generator 24 and performs a variety of image processing thereon. Otherwise, for example, the image processor 26 acquires an X-ray image generated by the image data generator 24 from the image data storage unit 25 and performs a variety of image processing thereon. The image processor 26 can also store image data subjected to image processing into the image data storage unit 25. The image processor 26 is also referred to as an image processing circuitry, and reads out a computer program corresponding to the above-described image processing function from the image data storage unit 25 and executes the computer program.

The input unit 22 is a control unit to be used by an operator (for example, a doctor or a technician) to operate the X-ray diagnostic apparatus, and accepts a variety of instructions from the operator. For example, the input unit 22 includes a mouse, a keyboard, a button, a trackball, a joystick, and a footswitch. The input unit 22 transfers the instructions accepted from the operator to the system controller 21 described later. The input unit 22 is also referred to as an input circuitry.

The display unit 23 has a monitor for displaying a graphical user interface (GUI) for accepting a command from the operator through the input unit 22 and for displaying X-ray images generated by the image data generator 24, X-ray images subjected to image processing by the image processor 26, and other images. The display unit 23 may display image data output by the image data generator 24 or the image processor 26 or may display image data acquired from the image data storage unit 25. The display unit 23 is also referred to as a display.

The system controller 21 controls the entire operation of the X-ray diagnostic apparatus 100. More specifically, the system controller 21 controls the high voltage generator 11, the C-arm/table mechanism controller 19, and the collimator controller 20 in accordance with a command from the operator that has been transferred from the input unit 22. The system controller 21 thus adjusts the X-ray dose, controls ON/OFF of X-ray irradiation, adjusts rotation and movement of the C-arm 15, and adjusts movement of the table 14. Additionally, the system controller 21 defines a certain region of interest on image data generated by the image data generator 24, and, based on a result of comparison between an average pixel value of the defined region of interest and a predetermined threshold, executes automatic brightness control (ABC).

Furthermore, the system controller 21 performs control over image generation processing in the image data generator 24 and image processing in the image processor 26 described below, in accordance with commands from the operator. The system controller 21 also performs control so that the GUI for accepting a command from an operator, X-ray images stored in the image data storage unit 25, and X-ray images subjected to image processing by the image processor 26 can be displayed on a monitor of the display unit 23. The system controller 21 is also referred to as a system control circuitry, and reads out a computer program corresponding to the above-described system controlling function from the image data storage unit 25 or the storage circuitry (not illustrated), and executes the computer program.

The overall configuration of the X-ray diagnostic apparatus 100 is as described above. This configuration enables the X-ray diagnostic apparatus 100 according to this embodiment to perform image display with a reduced processing time. Specifically, the X-ray diagnostic apparatus 100 can display, with a reduced processing time, X-ray images for which the visibility of a treatment tool (device) that is displayed during execution of endovascular intervention treatment, which is performed with reference to the X-ray images, is ensured.

For example, when conducting endovascular intervention treatment using a "balloon-tip catheter having a stent strut" for a stricture site in a blood vessel in the heart of the subject P, a doctor positions the device with reference to X-ray images generated by the X-ray diagnostic apparatus. As described above, when endovascular intervention treatment is conducted on a blood vessel in an organ such as the heart that always pulses or in an organ that moves because of pulsation, the position of the device in X-ray images moves.

It is therefore an extremely skillful task for doctors to position the device by referring to X-ray images.

Figure 2:
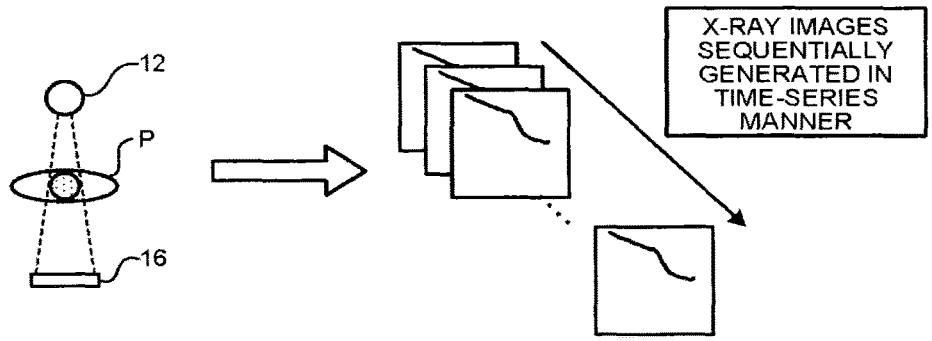
FIG. 2 is a diagram for explaining X-ray images to be subjected to processing.

In a conventional technique, moving images are displayed in which the device appears virtually stationary. Such display is enabled, for example, by tracking markers at two points visualized in the sequentially generated X-ray images and deforming the images such that the markers at two points in each X-ray image are located at the same positions as in the past images. For example, as illustrated in FIG. 2, the X-ray tube 12 emits X-rays to a region of interest (for example, the heart) of the subject P, and the X-ray detector 16 sequentially detects X-rays transmitted through the region of interest. The X-ray diagnostic apparatus 100 performs image processing based on data successively detected by the X-ray detector 16 such that a device contained in X-ray images sequentially generated in a time-series manner appears virtually stationary. The X-ray diagnostic apparatus 100 displays these X-ray images as moving images on a real-time basis. FIG. 2 is a diagram for explaining X-ray images to be subjected to the processing.

This processing enables the X-ray diagnostic apparatus 100 to display X-ray images for which the visibility of a device displayed therein during execution of endovascular intervention treatment performed with reference to the X-ray images is ensured, thereby enabling the X-ray diagnostic apparatus 100 to facilitate the positioning of the device. With the above-described technique, however, it requires considerable time to detect and identify (localize) the markers. Therefore, it sometimes requires considerable time to display moving images in which the device appears virtually stationary. In order to avoid this inconvenience, the X-ray diagnostic apparatus 100 according to the present application uses the system controller 21 to allow for a reduction in processing time for displaying moving images in which the device appears virtually stationary.

Figure 3:
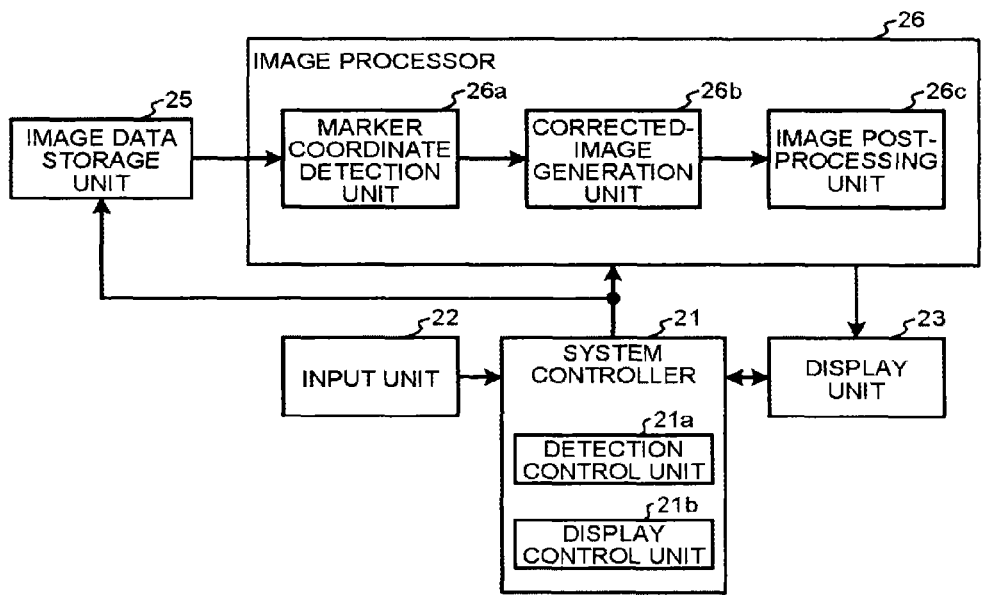
FIG. 3 is a diagram illustrating one example of the configuration of the image processor and the system controller according to the first embodiment.

Here, the following firstly describes processing that the image processor 26 performs for displaying moving images in which the device appears virtually stationary, and then describes control to be performed by the system controller 21 according to this embodiment. FIG. 3 is a diagram illustrating one example of the configuration of the image processor 26 and the system controller 21 according to the first embodiment. As illustrated in FIG. 3, the image processor 26 includes a marker coordinate detection unit 26a, a corrected-image generation unit 26b, and an image post-processing unit 26c. More specifically, an image processing circuitry, which executes the image processing function, reads out computer programs corresponding to functions of the marker coordinate detection unit 26a, the corrected-image generation unit 26b, and the image post-processing unit 26c from the image data storage unit 25 or the storage unit (not illustrated). The image processing circuitry then executes the computer programs, thereby executing functions described below.

Here, the image processor 26 is also referred to as a correction processor, where the marker coordinate detection unit 26a, the corrected-image generation unit 26b, and the image post-processing unit 26c generate moving images in which the device appears virtually stationary. Specifically, the image processor 26 executes first processing and second processing. The first processing is processing where, upon receiving an instruction to start correction processing, the image processor 26 obtains, as a reference position, the position of a target contained in a predetermined X-ray image. The second processing is processing where the image processor 26 sequentially generates corrected images by correcting newly generated X-ray images such that the target in the corrected images is positioned at the reference position. The following describes processing to be performed by the individual units included in the image processor 26.

The marker coordinate detection unit 26a localizes a predetermined target regarding a medical device inserted into the body of a subject by use of a cluster of X-ray images sequentially generated by the image data generator 24 within a predetermined period, and detects, based on the localization result, the positions of the predetermined target in newly generated X-ray images. Specifically, each time a new image, which is a new X-ray image, is stored into the image data storage unit 25, the marker coordinate detection unit 26a detects coordinate points of stent markers attached to a stent or a coordinate point of one point depending on the stent markers (for example, the midpoint therebetween) in the new image. For example, based on information on the stent markers visualized in images, the marker coordinate detection unit 26a detects the positions of the stent markers in sequentially generated X-ray images. In one illustrative example, based on information on stent markers designated by an operator or on a teacher image of the stent markers, the marker coordinate detection unit 26a detects the positions of the stent markers or the position of one point depending on the stent markers (for example, the midpoint therebetween) in sequentially generated X-ray images.

Figure 4A:
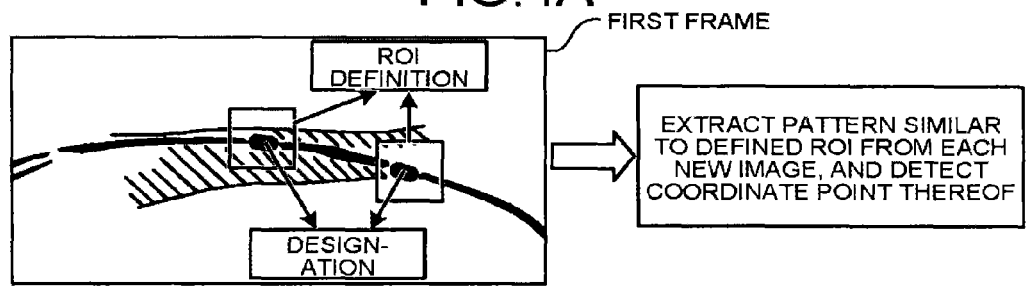
FIGS. 4A and 4B are diagrams for explaining processing that a marker coordinate detection unit according to the first embodiment performs.
Figure 4B:

The following describes an example of the case where positions of two stent markers are detected. FIGS. 4A and 4B are diagrams for explaining processing that the marker coordinate detection unit 26a according to the first embodiment performs. For example, as illustrated in FIG. 4A, the system controller 21 described below performs control such that an X-ray image (a first frame) stored in the image data storage unit 25 appears on a monitor of the display unit 23. An operator (such as a doctor), referring to the first frame, designates two stent markers in the first frame via the input unit 22, as illustrated in FIG. 4A. The marker coordinate detection unit 26a thus detects a coordinate point of each of the two stent markers in the first frame.

As illustrated in FIG. 4A, the marker coordinate detection unit 26a then defines, as a region of interest (ROI), a rectangle centering on a coordinate point of each of the two stent markers designated in the first frame, and extracts patterns that resemble a pattern in each of the defined ROIs from each of the sequentially generated new images, for example, by a cross-correlation method. The marker coordinate detection unit 26a detects, as a coordinate point of the stent marker, a coordinate point that has the highest cross-correlation value.

FIG. 4A illustrates a case where an operator designates two locations of stent markers. However, this embodiment is not limited to this case, and may include a case where an operator designates one location of a stent marker. In such a case, the marker coordinate detection unit 26a detects a coordinate point of the other stent marker even in the first frame by executing the cross-correlation method using an ROI defined based on a coordinate point of the designated stent marker.

Alternatively, the marker coordinate detection unit 26a uses a teacher image to detect a coordinate point of a stent marker. The teacher image represents shape and brightness characteristics to be exhibited in an X-ray image by a stent marker attached to a stent that is actually used in medical treatment. For example, as illustrated in FIG. 4B, with an X-ray image of a stent marker previously stored separately as a teacher image, the marker coordinate detection unit 26a extracts patterns resembling the teacher image from each new image, and searches for a region with the highest resemblance from the thus extracted candidate regions of the stent marker, thereby detecting the coordinate point of the stent marker.

Here, when detecting coordinate points of the stent marker from sequentially generated X-ray images, the marker coordinate detection unit 26a identifies (localizes) the stent marker by using a plurality of X-ray images. More specifically, using a cluster of X-ray images sequentially generated by the image data generator 24 within a predetermined period, the marker coordinate detection unit 26a localizes a predetermined target inserted into the body of a subject and visualized in X-ray images. Based on the localization result, the marker coordinate detection unit 26a then detects the positions of the predetermined target contained in newly generated X-ray images. For example, using a stent marker that has been designated by an operator or that is based on a teacher image, the marker coordinate detection unit 26a extracts, from each of a plurality of X-ray images within a predetermined period, all regions that resemble the stent marker. The marker coordinate detection unit 26a then extracts, as the stent marker, a region that is the most similar to the stent marker from the regions extracted from each of the X-ray images. In the following description, the above-described processing for detecting and identifying (localizing) a stent marker is referred to as a "Learning mode".

FIG. 5 is a diagram for explaining one example of the Learning mode according to the first embodiment. FIG. 5 illustrates the Learning mode where X-ray images corresponding to n frames are used, which have been generated by the image data generator 24. For example, the marker coordinate detection unit 26a extracts all regions (coordinate points) resembling a stent marker from the entire region of the first frame illustrated in FIG. 5. The marker coordinate detection unit 26a pairs each of all of the extracted coordinate points with each of the other ones thereof, and assigns a score to each of the pairs in accordance with such a factor as resemblance. For example, the marker coordinate detection unit 26a assigns a score to a pair of a coordinate point 51 and another coordinate point 52. Although FIG. 5 illustrates only the coordinate point 51 and the coordinate point 52, any other region (coordinate point) resembling the stent marker contained therein is detected and is paired with the coordinate point 51, with the coordinate point 52, and with any other coordinate point. Scores are then assigned to those pairs.

Likewise, the marker coordinate detection unit 26a performs the above-described processing with respect to each of the second to n-th frames, thereby assigning scores to individual pairs determined based on all of extracted coordinate points. The marker coordinate detection unit 26a then extracts, as the coordinate points of the stent markers, the coordinate points that give the highest score for each frame, and then extracts a region where the stent marker may be located in X-ray images in the predetermined period. For example, as illustrated in FIG. 5, the marker coordinate detection unit 26a extracts pairs of coordinate points 51 and coordinate points 52 that give the highest scores in the respective frames, and then extracts a region R1 where these coordinate points are included. The extraction of the region R1 is performed, for example, in such a manner that, after rectangles of a predetermined size each centering on the midpoint between the corresponding coordinate point 51 and the corresponding coordinate point 52 are extracted from the respective frames, a region that includes all of the extracted rectangles is extracted as the region R1.

For example, such movements as heartbeats and lung expansion/contraction continue in an orderly (periodic) manner, so that a stent marker, which moves following such movements, appears to move in an orderly (periodic) manner. In the above-described Learning mode, stent markers appearing to move in orderly manners (periodically) are exhaustively detected by use of the X-ray images within the predetermined period, one of those stent markers that resembles the stent marker most is identified (localized) as the stent marker. In the Learning mode, for example, X-ray images corresponding to around 40 frames are used.

As described above, the marker coordinate detection unit 26a performs the Learning mode, so that it identifies (localizes) the stent marker in the X-ray images and extracts a region including positions where the stent marker may be located. The marker coordinate detection unit 26a then sets the extracted region as the target region, and detects the stent marker from the target region. For example, the marker coordinate detection unit 26a performs processing for detecting the stent marker in X-ray images newly generated from within the region R1 illustrated in FIG. 5 with this region set as a target region of the processing.

Figure 6A:
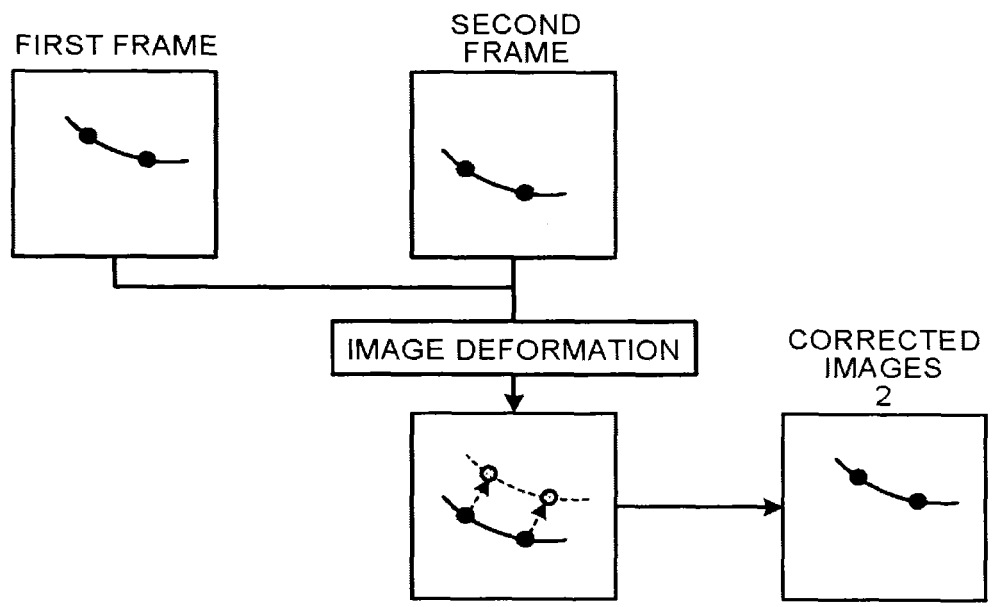
FIGS. 6A and 6B are diagrams for explaining processing that a corrected-image generation unit according to the first embodiment performs.
Figure 6B:
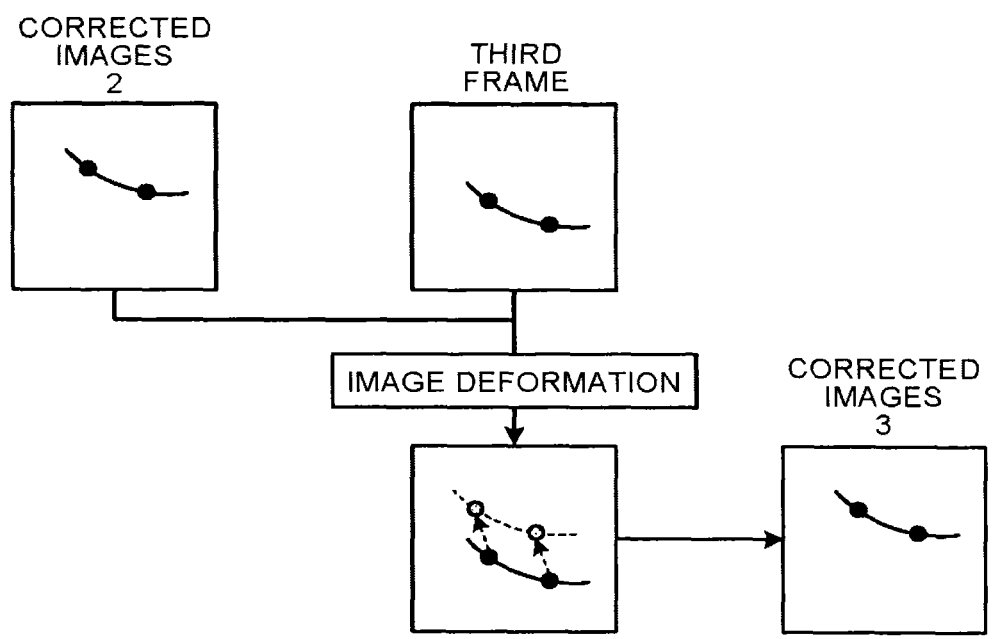

Back to FIG. 3, the corrected-image generation unit 26b sets, as reference coordinate points, the coordinate point of the stent marker that has already been detected by the marker coordinate detection unit 26a. The corrected-image generation unit 26b generates corrected images by performing image displacement such as translation and rotation, and image deformation such as affine transform on new images so that the coordinate points of the stent marker that have been detected by the marker coordinate detection unit 26a in the new images can be the same coordinate points as the reference coordinate point. FIGS. 6A and 6B are diagrams for explaining processing that the corrected-image generation unit 26b according to the first embodiment performs. FIGS. 6A and 6B illustrate processing on a new image from which the coordinate point of the stent marker has been detected based on the processing result of the Learning mode after the marker coordinate detection unit 26a has completed the processing of the Learning mode. More specifically, the first frame illustrated in FIGS. 6A and 6B refers to an X-ray image generated first after the completion of the Learning mode.

For example, the marker coordinate detection unit 26a first executes the processing of Learning mode by using images corresponding to 40 frames. As illustrated in FIG. 6A, the marker coordinate detection unit 26a then detects the coordinate points of the stent marker from the first frame and the second frame that have been generated after the completion of the Learning mode, by using the processing result of the Learning mode. When the marker coordinate detection unit 26a has detected the coordinate points of the stent marker, as illustrated in FIG. 6A, the corrected-image generation unit 26b generates a corrected image 2 from the second frame through image deformation so that the coordinate point of the stent marker, detected in an X-ray image corresponding to the second frame generated as a new image, can be the same as the coordinate point (reference position) of the stent marker that has been already detected in the first frame. The corrected-image generation unit 26b then generates a corrected image with respect to a new image corresponding to each of the third and subsequent frames by using, as the reference position (reference coordinate point), the coordinate point of the stent marker in a corrected image generated by the corrected-image generation unit 26b from an X-ray image generated immediately before the new image. For example, as illustrated in FIG. 6B, the corrected-image generation unit 26b generates a corrected image 3 from the third frame by performing image deformation such that the coordinate point of the stent marker detected from the third frame can be the same as the coordinate point of the stent marker in the corrected image 2 generated from the second frame.

In the above description, the embodiment is configured such that the coordinate point of the stent marker in a corrected image generated from a frame immediately before a new image is used as the reference coordinate point. Embodiments are not limited to this configuration, and may be configured such that corrected images from new images corresponding to the second and subsequent frames are generated while the coordinate point of the stent marker detected in the first frame is constantly used as the reference coordinate point. However, as described below, corrected images are used for generating images to be displayed in display of moving images. To reliably execute display of moving images in which the position of the stent marker is invariable, it is therefore desirable that a corrected image be generated from a new image by use of an immediately preceding corrected image.

As described above, the corrected-image generation unit 26b generates corrected images in which the coordinate points of the stent marker detected by the marker coordinate detection unit 26a are set to the same coordinate point. More specifically, after the stent marker is identified through the Learning mode, the corrected-image generation unit 26b generates corrected images in which the coordinate points of the stent marker detected from succeeding X-ray images are set to the same coordinate point, by using the processing result of the Learning mode. In the following description, the above-described processing to generate corrected images is referred to as a "Tracking mode".

Figure 7:
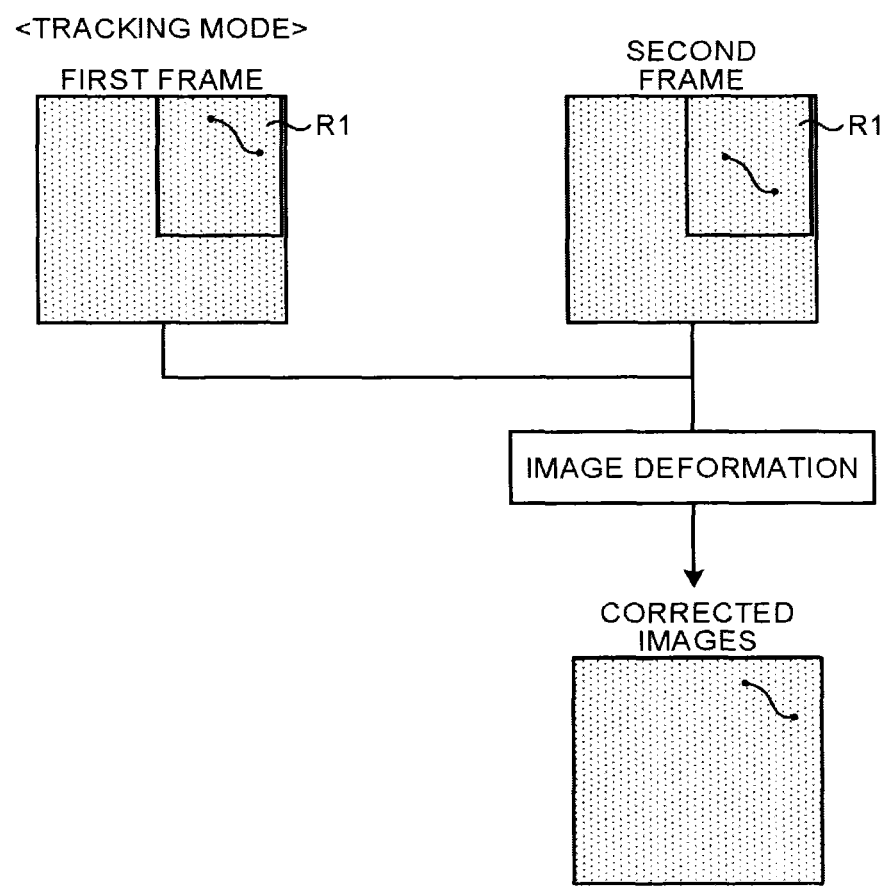
FIG. 7 is a diagram for explaining one example of a Tracking mode according to the first embodiment.

FIG. 7 is a diagram for explaining one example of the Tracking mode according to the first embodiment. For example, in the Tracking mode, as illustrated in FIG. 7, corrected images are generated through image deformation such that the positions of a stent marker detected within the region R1 extracted through the Learning mode are set at the same position. More specifically, the corrected-image generation unit 26b generates corrected images for X-ray images from which the stent marker is detected by the marker coordinate detection unit 26a after the Learning mode.

Figure 8:
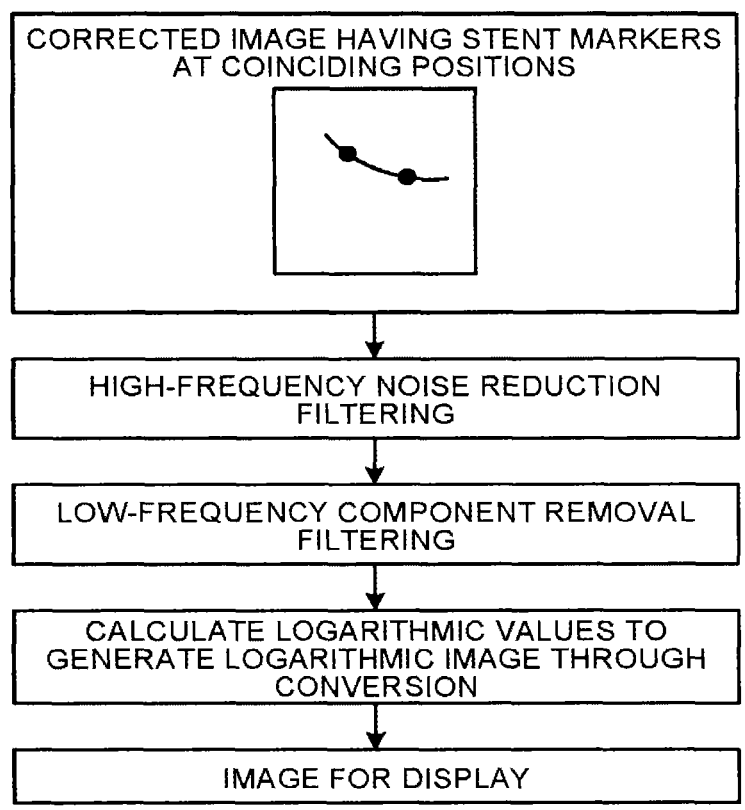
FIG. 8 is a diagram for explaining one example of processing that an image post-processing unit according to the first embodiment performs.

Back to FIG. 3, the image post-processing unit 26c performs post-processing on corrected images generated by the corrected-image generation unit 26b. FIG. 8 is a diagram for explaining one example of processing that the image post-processing unit 26c according to the first embodiment performs. For example, as illustrated in FIG. 8, the image post-processing unit 26c generates a filtered corrected image by executing high-frequency noise reduction filtering and low-frequency component removal filtering on a corrected image having the stent marker at the same position as the first frame. The image post-processing unit 26c further generates a logarithmic image by calculating natural logarithmic values of the pixel values of the respective pixels included in the filtered corrected image. The image post-processing unit 26c executes the above-described post-processing also with respect to the first frame.

Here, the image post-processing unit 26c performs high-frequency noise reduction processing using a spatial filter that is described, for example, in the following documents: Nambu, H. Iseki, "A noise reduction method based on a statistical test of high dimensional pixel vectors for dynamic and volumetric images", Riv Neuroradiol 2005, 18:21-33; and Nishiki, "Method for reducing noise in X-ray images by averaging pixels based on the normalized difference with the relevant pixel", Radiological Physics and Technology, Vol. 2, 2008.

This spatial filter applies high-frequency noise reduction processing in which: differences in pixel value between frames of different points in time are measured; while different weights are assigned according to the magnitudes of the differences, smoothening is performed within a single frame. This filter can reduce high-frequency noise without affecting other frames. Here, because corrected images have the stent marker located at the same coordinate point, the spatial filter can be applied exhaustively, thereby reducing high-frequency noise in a portion corresponding to the stent and allowing for enhanced visibility of the stent in the corrected images.

Alternatively, the image post-processing unit 26c may execute high-frequency noise reduction filtering using, for example, a recursive filter is applied. A recursive filter is a filter that reduces high-frequency noise by adding, to pixel values of the pixels included in a frame to be filtered, pixel values of the pixels included in a past frame to which predetermined weights are assigned. Because corrected images have the stent marker at the same coordinate point, a recursive filter, where a past frame is used for the filtering, also reduces high-frequency noise in a portion corresponding to the stent, thereby allowing for enhanced visibility of the stent in the corrected images.

The image post-processing unit 26c performs low-frequency component removal filtering with a high-pass filter. The contrast thus can be reduced in a background portion in each of the corrected images, which is a portion other than the stent portion. The image post-processing unit 26c further performs processing to generate a logarithmic image on a filtered corrected image, thereby allowing each component of a signal to be constant throughout an image.

The above description covers the processing that the image processor 26 performs when displaying moving images in which the device appears virtually stationary. The following describes the system controller 21 according to the first embodiment. As illustrated in FIG. 3, the system controller 21 includes a detection control unit 21a and a display control unit 21b. More specifically, a system control circuitry, which executes the system controlling function, reads out computer programs corresponding to functions of the detection control unit 21a and the display control unit 21b from the image data storage unit 25 or the storage unit (not illustrated). The image processing circuitry then executes the computer programs, thereby executing functions described below. Here, the detection control unit 21a controls the above-described image processor 26 to reduce a processing time for displaying moving images in which the device appears virtually stationary. The details of this processing are to be described later.

Each time the image post-processing unit 26c newly generates a logarithmic image in a time-series manner, the display control unit 21b performs control to sequentially display the newly generated logarithmic image, as an image to be displayed, on the monitor of the display unit 23. More specifically, the display control unit 21b performs control to display, as moving images, images to be displayed (stent-fixed images) in which the coordinate points of the stent marker are located at the same position. Although the background portion other than the stent portion is blurred as a result, X-ray images can be displayed as moving images with the stent portion appearing stationary.

Here, the display control unit 21b displays the stent-fixed images in any one of various forms according to a display-form instruction command received from an operator via the input unit 22. Specifically, the display control unit 21*b* performs control, according to the display-form instruction command, to display defined regions as the stent-fixed images. The defined regions are determined based on the coordinate points of the stent marker in the logarithmic images. For example, when the coordinate points of two stent markers in a logarithmic image are (X1,Y1) and (X2,Y2), the display control unit 21*b* sets up, as the defined region, a rectangular region centering on ((X1+X2)/2,(Y1+Y2)/2) and having a width of "2×|X1−X2|" and a height of "2×|Y1−Y2|". The display control unit 21*b* then performs control to display the logarithmic image while masking a region thereof other than the defined region.

The display control unit 21*b* performs control to display enlarged images obtained by enlarging the defined regions as the stent-fixed images. Here, when the stent-fixed images only of one kind, i.e., the logarithmic images, the defined regions, or the enlarged images, are exclusively displayed, the display control unit 21*b* performs control to put the positions of the stent marker in these stent-fixed images at the center of the monitor of the display unit 23. Alternatively, the display control unit 21*b* performs control according to the display-form instruction command so that original images of images to be displayed may be displayed in parallel with the stent-fixed images. Here, when these images are displayed in parallel, if the defined regions or the enlarged images are stent-fixed images, the display control unit 21*b* performs control to display, as original images, regions corresponding to the defined regions.

Figure 9A:
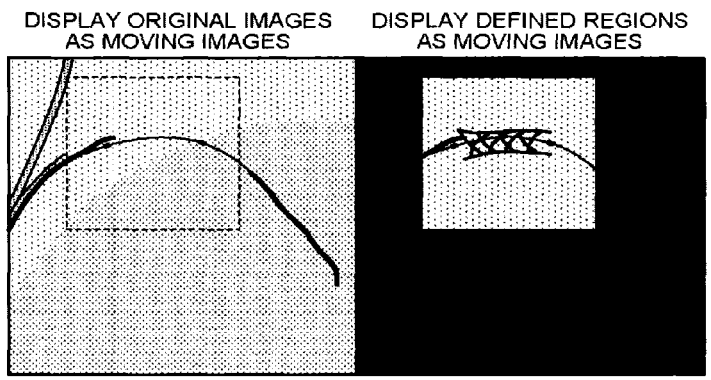
FIGS. 9A and 9B are diagrams illustrating one example of moving images that a display controller according to the first embodiment displays.
Figure 9B:
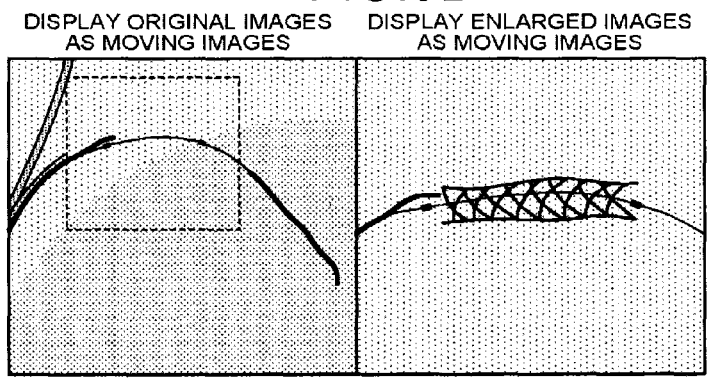

FIGS. 9A and 9B are diagrams illustrating one example of moving images that the display control unit 21*b* according to the first embodiment displays. For example, as illustrated in FIG. 9A, the display control unit 21*b* performs control to display original images as moving images and the defined regions as moving images in parallel on the monitor of the display unit 23. The original images have boundaries added thereon that correspond to the defined regions. Otherwise, as illustrated in FIG. 9B, the display control unit 21*b* performs control to display original images as moving images and the enlarged images as moving images in parallel on the monitor of the display unit 23. The original images have boundaries added thereon that correspond to the defined regions.

Here, in each of the defined regions and each of the enlarged images, as illustrated in FIGS. 9A and 9B, the stent strut appears more clearly, and the contrast in the background portion is weaker, than in original images thereof as a result of the above-described post-processing. The entire stent is thus more visible. The boundaries on such original images move following the move of the position of stent marker. The original images and the stent-fixed images may be displayed in parallel as described above on one monitor included in the display unit 23. Alternatively, the display unit 23 that includes a plurality of monitors may display each of the original images and each of the stent-fixed images on two different monitors.

Described above is a case where this embodiment is configured to set logarithmic images, defined region, or enlarged images as stent-fixed images. However, this embodiment is not limited to this case, However, this embodiment is not limited to this case, and may be such that the corrected images as they are, or images subjected to a desirable combination of two or more kinds of post-processing selected from high-frequency noise reduction filtering, low-frequency component removal filtering, and logarithmic-image generation processing are used as images to be displayed, which has been set by an operator.

As described above, the X-ray diagnostic apparatus 100 identifies a stent marker through the Learning mode with a plurality of X-ray images, and detects the stent marker in succeeding X-ray images, based on the identification result. The X-ray diagnostic apparatus 100 then generates stent-fixed images through the Tracking mode and displays the stent-fixed images as moving images. Here, a conventional X-ray diagnostic apparatus executes processing from the Learning mode each time fluoroscopy or radiography is executed, therefore requiring a long time to display moving images in which the device appears virtually stationary.

Figure 10:
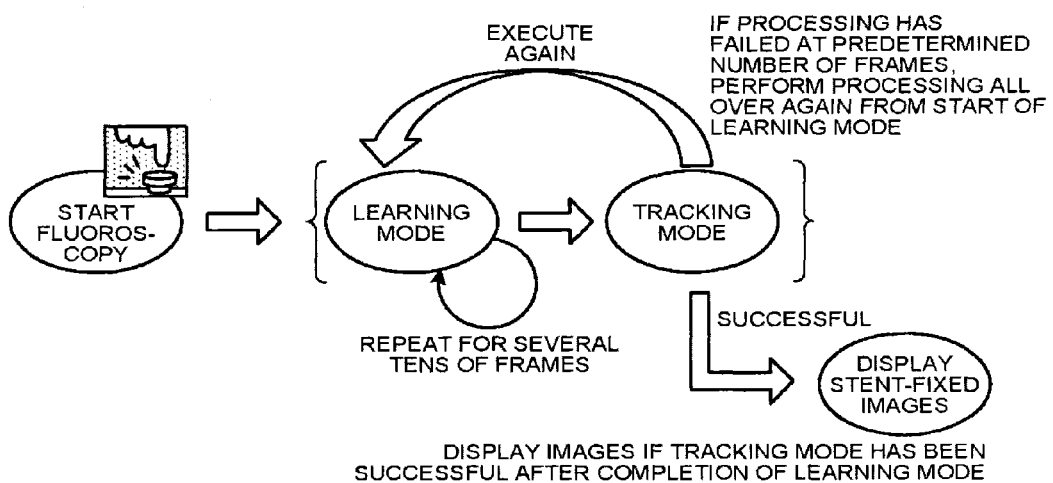
FIG. 10 is a diagram for explaining one example of inconveniences associated with a conventional technique.

FIG. 10 is a diagram for explaining one example of inconveniences associated with a conventional technique. For example, as illustrated in FIG. 10, when fluoroscopy is started, an X-ray diagnostic apparatus according to a conventional technique identifies a stent marker through the Learning mode where several tens of frames are repeatedly used, and then proceeds to the Tracking mode. Subsequently, in the X-ray diagnostic apparatus according to a conventional technique, stent-fixed images are displayed upon successful completion of the Tracking mode. In the X-ray diagnostic apparatus according to a conventional technique, processing of the Learning mode and subsequent processing are performed all over again when processing failures have occurred at a predetermined number of frames in the Tracking mode.

As described above, the X-ray diagnostic apparatus according to a conventional technique performs the same processing, for example, each time fluoroscopy is started, therefore regularly requiring a certain length of time to display stent-fixed images, and further, if processing has failed in the Tracking mode, requires time to return to processing because of the need to perform processing all over again from the Learning mode. To eliminate this inconvenience, the X-ray diagnostic apparatus 100 according to the first embodiment causes the detection control unit 21*a* and the display control unit 21*b* to perform control to reduce a processing time for displaying the stent-fixed images.

Specifically, in accordance with manipulation performed on a subject, the detection control unit 21*a* controls processing (the Learning mode) that the marker coordinate detection unit 26*a* performs to localize a predetermined target. More specifically, when a plurality of sequentially generated clusters of X-ray images are generated by the image data generator 24, the detection control unit 21*a* performs control so that, on condition that the conditions of manipulation on a subject are uniform among the clusters, processing to detect a predetermined target from a more-recently generated cluster of X-ray images can be executed based on the result of localization (processing result of the Learning mode) with respect to the predetermined target where an earlier generated cluster of X-ray images is used. Here, examples of the predetermined target include: each of the above-described two stent markers; and one point depending on the two stent markers (for example, the midpoint therebetween). More specifically, the detection control unit 21*a* controls processing of the Learning mode that the marker coordinate detection unit 26*a* performs to identify each of the above-described two stent markers; and one point depending on the two stent markers.

Figure 11A:
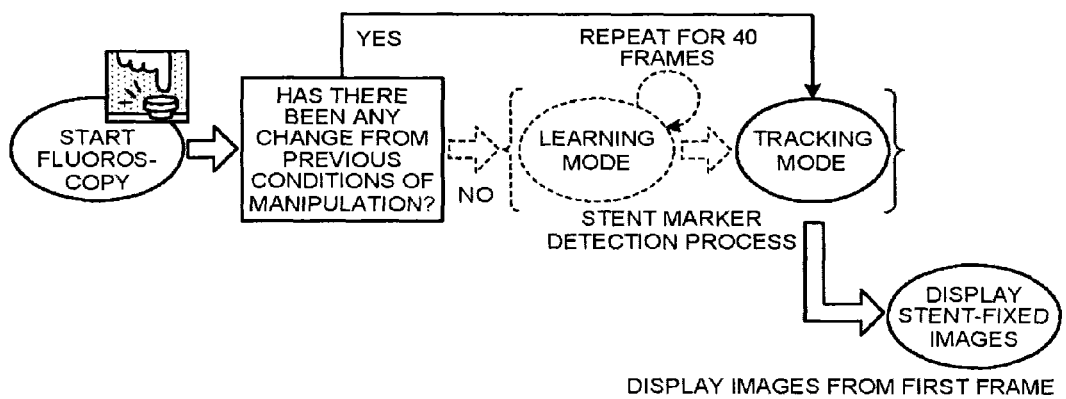
FIG. 11A is a diagram for explaining one example of processing that a detection control unit according to the first embodiment performs.

FIG. 11A is a diagram for explaining one example of processing that the detection control unit 21*a* according to the first embodiment performs. For example, when brief fluoroscopy such as ablation is performed successively (a plurality of times), the detection control unit 21*a* determines whether there has been any change in the previous manipulation conditions, as illustrated in FIG. 11A. This determination is made after the start of fluoroscopy, before execution of stent marker detection processing composed of the Learning mode and the Tracking mode. For example, the detection control unit 21a determines whether there has been any change in such conditions as the angle of the C-arm 15, the height of the couch, the field of view (FOV), and the SID. If the detection control unit 21a determines that there has been no change therein, the detection control unit 21a performs control to skip the Learning mode and execute the Tracking mode.

More specifically, the detection control unit 21a controls the marker coordinate detection unit 26a so that a stent marker in a newly generated X-ray image can be detected based on the result of the Learning mode applied to previous fluoroscopy. The corrected-image generation unit 26b generates corrected images based on the coordinate points of the stent marker that have been detected by the marker coordinate detection unit 26a by use of the previous result of the Learning mode. In manipulation such as ablation, fluoroscopy is turned on and off with the various conditions being unchanged. Therefore, accuracy of detection of a stent marker is not affected even when the result of the Learning mode performed in fluoroscopy conducted the first time is used in fluoroscopy conducted later. As described above, control is performed so that the Tracking mode can be executed with the Learning mode skipped, whereby a time corresponding to the Learning mode using X-ray images corresponding to several tens of frames (for example, 40 frames) can be omitted. The corresponding processing time is reduced to enable immediate display of stent-fixed images. In other words, the X-ray diagnostic apparatus 100 according to the first embodiment can display a stent-fixed image from the first frame after fluoroscopy is started. Furthermore, X-ray images corresponding to several tens of frames of Learning mode are not needed, whereby radiation exposure can be reduced by the amount corresponding to these X-ray images.

The following describes specifics of processing. Under the control of detection control unit 21a, the marker coordinate detection unit 26a stores, into the image data storage unit 25 or the storage unit (not illustrated), a result of the Learning mode executed with respect to each set of the conditions of manipulation on a subject. Upon receiving an instruction to start correction processing, the corrected-image generation unit 26b then executes the Tracking mode in accordance with the condition of manipulation on a subject by use of information on the reference position stored in the image data storage unit 25 or the storage unit (not illustrated).

Figure 11B:
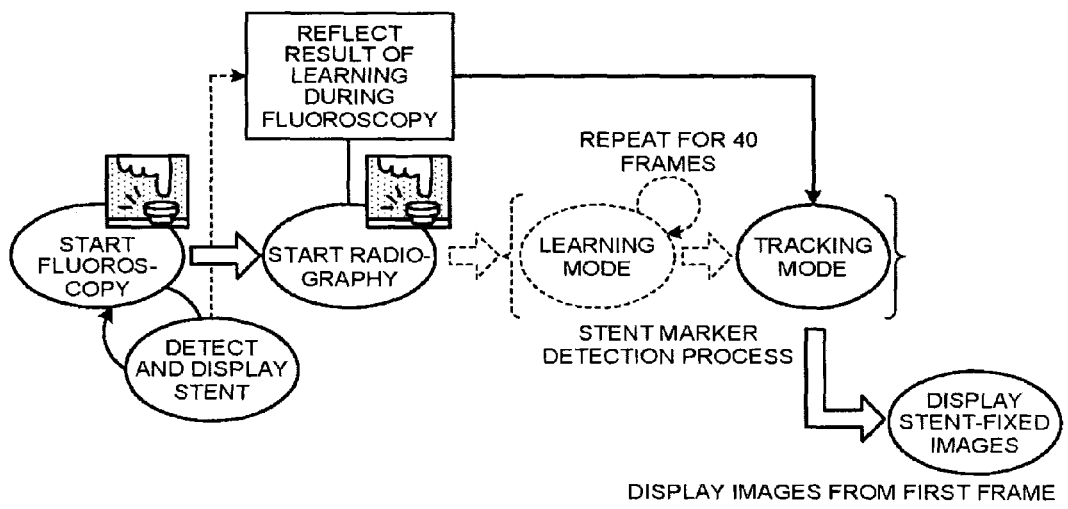
FIG. 11B is a diagram for explaining one example of processing that the detection control unit according to the first embodiment performs.

The above-described processing is also applicable to radiography where generated X-ray images are saved. More specifically, the detection control unit 21a performs control so that, when a cluster of X-ray images is generated through radiography for saving X-ray images, processing to detect a predetermined target (a stent marker) from a cluster of X-ray images generated by the radiography can be performed based on the result of the Learning mode with respect to the stent marker where a cluster of X-ray images generated in immediately preceding fluoroscopy is used. FIG. 11B is a diagram for explaining one example of processing that the detection control unit 21a according to the first embodiment performs.

For example, in general, fluoroscopy is performed for checking surrounding sites immediately before radiography is performed. Radiography is then performed without any change in conditions such as the angle of the C-arm 15, the height of the couch, the FOV, and the SID. The detection control unit 21a then controls the marker coordinate detection unit 26a so that the Learning mode can be executed at the start of the fluoroscopy prior to radiography, as illustrated in FIG. 11B. Subsequently, after the radiography is started, the detection control unit 21a performs control so that the Tracking mode can be executed with the Learning mode in the stent marker detection processing skipped.

More specifically, the detection control unit 21a controls the marker coordinate detection unit 26a so that a stent marker in a newly generated X-ray image can be detected based on the result of the Learning mode executed at fluoroscopy. The corrected-image generation unit 26b generates corrected images based on the coordinate points of the stent marker that have been detected by the marker coordinate detection unit 26a by use of a result of the Learning mode at the fluoroscopy. The X-ray diagnostic apparatus 100 according to the first embodiment thus can (display a stent-fixed image from the first frame after fluoroscopy is started) immediately display a stent-fixed image with a reduced processing time even in such a situation. The X-ray diagnostic apparatus 100 can also reduce radiation exposure.

As described above, the display control unit 21b controls a moving image display of original images and stent-fixed images. Here, in addition to the above-described moving image display, the display control unit 21b according to the first embodiment can also control to display, on the display unit 23, information indicating a status of the stent marker detection processing. Specifically, the display control unit 21b controls to display, on the display unit 23, at least one of the success/failure results of: processing of the Learning mode by the marker coordinate detection unit 26a; processing of the Tracking mode by the corrected-image generation unit 26b; and the corrected-image generation processing.

Figure 12:
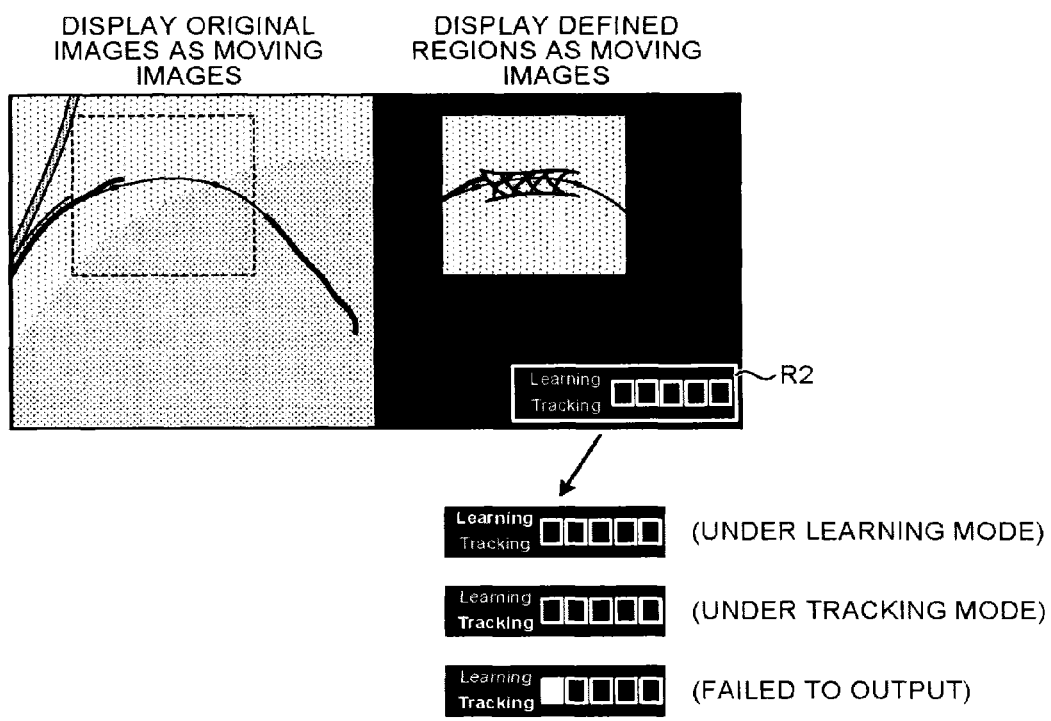
FIG. 12 is a diagram illustrating one example of processing that the display controller according to the first embodiment performs.

FIG. 12 is a diagram illustrating one example of processing that the display control unit 21b according to the first embodiment performs. For example, as illustrated in FIG. 12, the display control unit 21b performs control so that a status of the stent marker detection processing can be displayed in a region R2 located in the lower part of each stent-fixed image. Here, for example, as illustrated in the illustrations in the lower part of FIG. 12, the display control unit 21b turns on "Learning" during the Learning mode and turns on "Tracking" during the Tracking mode. When outputting stent-fixed images has failed at the Tracking mode, the display control unit 21b further turns on an indicator in a progress bar or the like illustrated in FIG. 12.

As described above, the X-ray diagnostic apparatus 100 is configured to execute the Learning mode again when displaying stent-fixed images has failed a plurality of times at the Tracking mode. For this reason, the display control unit 21b turns on one of the indicators illustrated in FIG. 12 each time outputting stent-fixed images fails. The display control unit 21b then turns off all of the turned-on indicators when stent-fixed images are successfully output before the number of times the outputting has been attempted reaches a predetermined number of times the outputting is allowed to fail. More specifically, the display control unit 21b sequentially turns on the indicators in order from the left to the right in FIG. 12, one at each time outputting stent-fixed images fails, and then turns off all of the indicators when stent-fixed images are successfully output. When the Learning mode is executed again after the number of times the outputting stent-fixed images has failed has reached the predetermined number of times the outputting is allowed to fail, the display control unit 21b turns off "Tracking" and all of the indicators and turns on "Learning".

The above-described example illustrates a case where the indicators are turned on as a result of the failure. However, embodiments are not limited to this case. For example, the control may be such that, after all of the indicators are turned on, the indicators are turned off, one at each time outputting stent-fixed images fails. For example, the display control unit 21b sequentially turns off the indicators in order from the left to the right (or from the right to the left) in FIG. 12, one at each time outputting stent-fixed images fails, and then turns on all of the indicators when stent-fixed images have been successfully output. Additionally, how the respective modes are displayed is not limited to the above-described example. For example, the control may be such that only a mode currently applied is displayed. More specifically, the display control unit 21b displays only "Learning" during the Learning mode and displays only "Tracking" during the Tracking mode.

Figure 13:
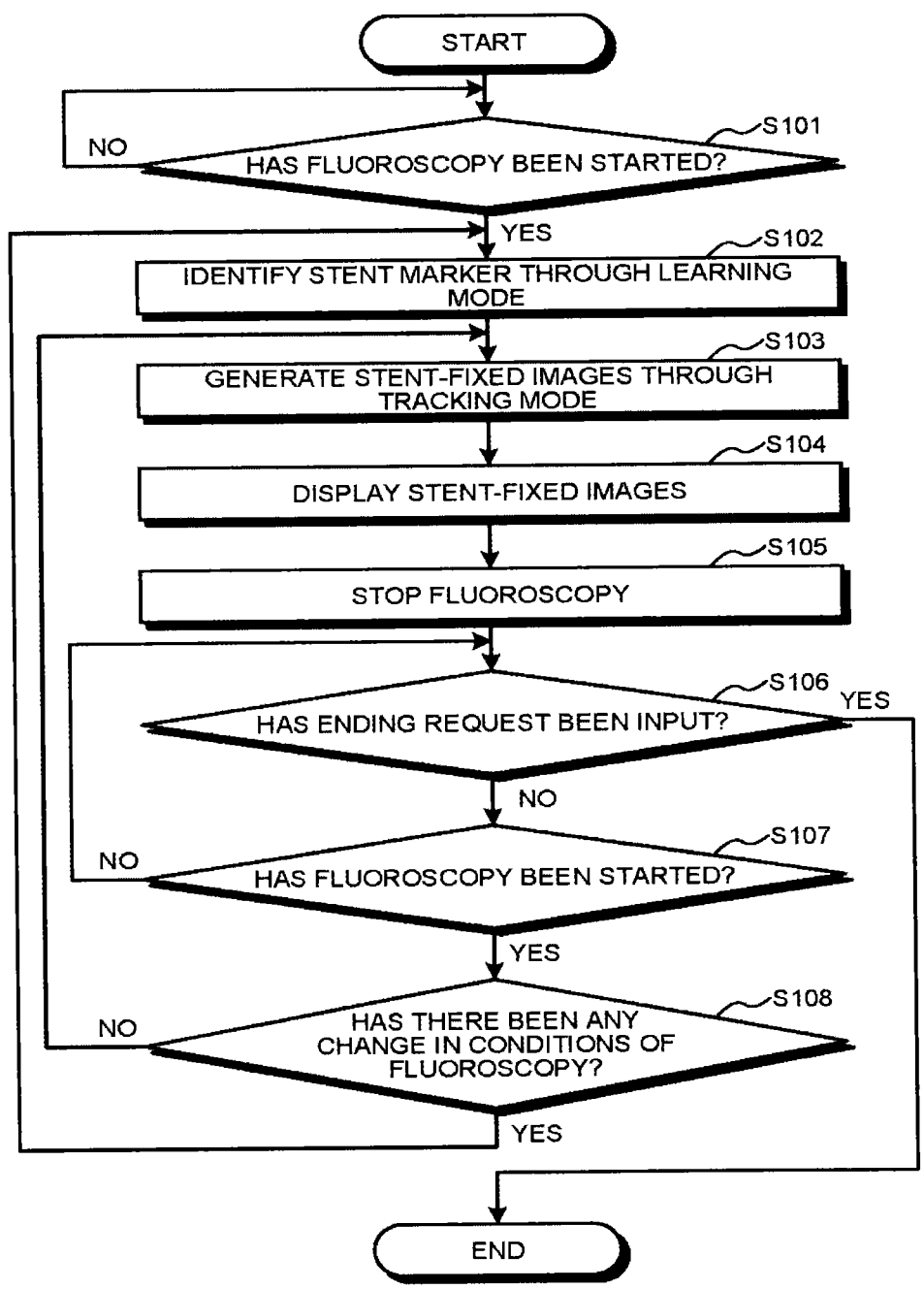
FIG. 13 is a flowchart illustrating a procedure of processing in the X-ray diagnostic apparatus according to the first embodiment.
Figure 14:
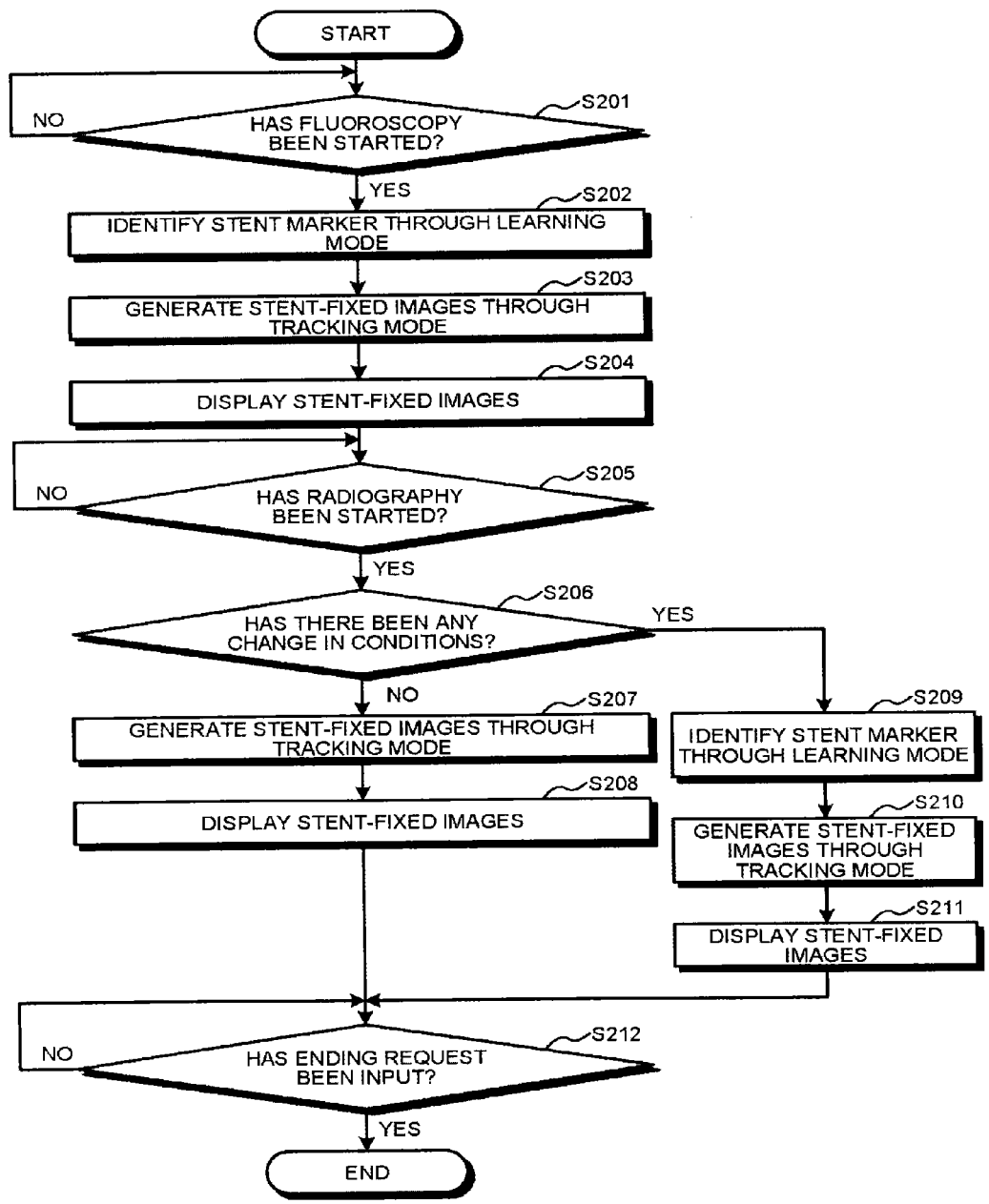
FIG. 14 is a flowchart illustrating a procedure of processing in the X-ray diagnostic apparatus according to the first embodiment.

The following describes procedures of processing in the X-ray diagnostic apparatus 100 with reference to FIG. 13 and FIG. 14. FIG. 13 and FIG. 14 are flowcharts illustrating procedures of processing in the X-ray diagnostic apparatus 100 according to the first embodiment. Here, while FIG. 13 represents a procedure of processing depending on whether there has been a change in the conditions of manipulation, FIG. 14 represents a procedure of processing in the case of radiography. The following procedures of processing are illustrated as applying to a case where a stent marker is identified and detected as a predetermined target.

As illustrated in FIG. 13, in the X-ray diagnostic apparatus 100 according to the first embodiment, when fluoroscopy is started (Yes at Step S101), the marker coordinate detection unit 26a identifies the stent marker through the Learning mode (Step S102). When the stent marker in new X-ray images is detected based on the identification result from the marker coordinate detection unit 26a, the corrected-image generation unit 26b generates stent-fixed images through the Tracking mode (Step S103), and the display control unit 21b displays the stent-fixed images on the display unit (Step S104).

When the fluoroscopy is then terminated under the operation from an operator (Step S105), the X-ray diagnostic apparatus 100 determines whether an ending request has been input (Step S106). Here, if the ending request has not been input (No at Step S106), the detection control unit 21a determines whether fluoroscopy has been started (Step S107). Here, if fluoroscopy has not been started (No at Step S107), the X-ray diagnostic apparatus 100 determines whether the ending request has been input (Step S106).

By contrast, if fluoroscopy has been started (Yes at Step S107), the detection control unit 21a determines whether any condition of fluoroscopy has been changed (Step S106). Here, if no condition of fluoroscopy has been changed (No at Step S108), the detection control unit 21a controls the marker coordinate detection unit 26a so that the stent marker can be detected by use of the result of the previous Learning mode, and the corrected-image generation unit 26b generates stent-fixed images through the Tracking mode, based on the detection result (Step S103).

By contrast, if any condition of fluoroscopy has been changed (Yes at Step S108), the detection control unit 21a returns to Step S102 to control the marker coordinate detection unit 26a to execute the Learning mode again.

The following describes the procedure of processing in the case of radiography. As illustrated in FIG. 14, in the X-ray diagnostic apparatus 100 according to the first embodiment, when fluoroscopy is started (Yes at Step S201), the marker coordinate detection unit 26a identifies the stent marker through the Learning mode (Step S202). When the stent marker in new X-ray images is then detected based on the identification result from the marker coordinate detection unit 26a, the corrected-image generation unit 26b generates stent-fixed images through the Tracking mode (Step S203), and the display control unit 21b displays the stent-fixed images on the display unit (Step S204).

If radiography has been started (Yes at step S205), the detection control unit 21a determines whether there has been any change in the conditions of manipulation (step S206). Here, if there has been no change in the conditions (No at Step S206), the detection control unit 21a controls the marker coordinate detection unit 26a to detect the stent marker by use of the result of the Learning mode at the fluoroscopy, the corrected-image generation unit 26b generates stent-fixed images through the Tracking mode, based on the detection result (Step S207), and the display control unit 21b displays the stent-fixed images on the display unit (Step S208).

By contrast, if there has been any change in the conditions of manipulation (Yes at Step S206), the marker coordinate detection unit 26a identifies the stent marker by executing processing of the Learning mode again (Step S209). When the stent marker in new X-ray images is then detected based on the new identification result from the marker coordinate detection unit 26a, the corrected-image generation unit 26b generates stent-fixed images through the Tracking mode (Step S210), and the display control unit 21b displays the stent-fixed images on the display unit (Step S211).

When stent-fixed images are displayed in Step S208 or Step S211, the X-ray diagnostic apparatus 100 determines whether an ending request has been input (Step S212). Here, if the ending request has not been input (No at Step S212), the display control unit 21b continues to have the stent-fixed images displayed. By contrast, if the ending request has been input (Yes at Step S212), the processing is ended.

As described above, according to the first embodiment, the image data generator 24 sequentially generates X-ray images based on X-rays emitted from the X-ray tube 12 and transmitted through the subject. Using a cluster of X-ray images sequentially generated by the image data generator 24 within a predetermined period, the marker coordinate detection unit 26a localizes a stent marker inserted into the body of the subject and visualized in X-ray images. Based on the localization result, the marker coordinate detection unit 26a then detects the position of the stent marker contained in newly generated X-ray images. The corrected-image generation unit 26b sets, as a reference position, the position of the stent marker detected from a reference image. The reference image is a predetermined X-ray image. The corrected-image generation unit 26b sequentially generates corrected images, which are obtained by subjecting newly generated X-ray images to correction processing where the positions of the stent marker detected in the newly generated X-ray images are set to the reference position. In accordance with manipulation performed on a subject, the detection control unit 21a controls processing of the Learning mode that the marker coordinate detection unit 26a performs on the stent marker. The display control unit 21b displays on the display unit 23, as moving images, corrected images sequentially generated by the corrected-image generation unit 26b. The X-ray diagnostic apparatus 100 according to the first embodiment thus can control whether to execute the Learning mode in accordance with kinds of manipulation, thereby allowing a reduction in processing time. Furthermore, the X-ray diagnostic apparatus 100 skips the Learning mode, thereby enabling reduction in radiation exposure.

According to the first embodiment, when a plurality of sequentially generated clusters of X-ray images are generated by the image data generator 24, the detection control unit 21a performs control so that, on condition that the clusters have common conditions of manipulation on a subject, processing to detect a stent marker from a more-recently generated cluster of X-ray images can be executed based on the result of the Learning mode using an earlier generated cluster of X-ray images with respect to the stent marker. Thus, the X-ray diagnostic apparatus 100 according to the first embodiment allows a reduction in processing time without impairing the detection accuracy for a stent marker.

According to the first embodiment, the detection control unit 21a performs control so that, when a cluster of X-ray images is generated through radiography for saving X-ray images, detection of a stent maker from a cluster of X-ray images generated by the radiography can be processed based on the result of the Learning mode with respect to the stent marker where a cluster of X-ray images generated in immediately preceding fluoroscopy is used. The X-ray diagnostic apparatus 100 according to the first embodiment thus allows a reduction in processing time for radiography.

According to the first embodiment, the display control unit 21b controls so that the display unit 23 can display thereon at least one of the success/failure results of: the Learning mode by the marker coordinate detection unit 26a; the Tracking mode by the corrected-image generation unit 26b; and the corrected-image generation processing. The X-ray diagnostic apparatus 100 according to the first embodiment thus enables presentation to an operator about what status the stent marker detection processing is currently in.

Second Embodiment

Described in the above-described first embodiment is a case where the result of the Learning mode performed earlier is used for execution of the Tracking mode to be performed thereafter. Described in a second embodiment is a case where execution of the Learning mode is continued during manipulation. The second embodiment is different from the first embodiment in specific contents of control that the detection control unit 21a performs. The following description centers on this difference. The following description uses a stent marker as an example of a predetermined target.

According to the second embodiment, while the image data generator 24 is generating X-ray images, the detection control unit 21a performs control so that processing of the Learning mode that the marker coordinate detection unit 26a performs on the stent marker can be continuously executed, and also performs control so that, if the corrected-image generation unit 26b has failed in generating corrected images, the positions of the stent marker contained in X-ray images newly generated can be detected based on a localization result of the localization processing continuously executed. More specifically, the detection control unit 21a does not perform control so that the Learning mode performed by the marker coordinate detection unit 26a may end after several tens of frames. The detection control unit 21a performs controls so that, the Learning mode can be continued during the entirety of manipulation in the background, and, if outputting stent-fixed images has failed at the Tracking mode, the coordinate point of the stent marker can be detected by use of the processing result of the Learning mode.

Figure 15:
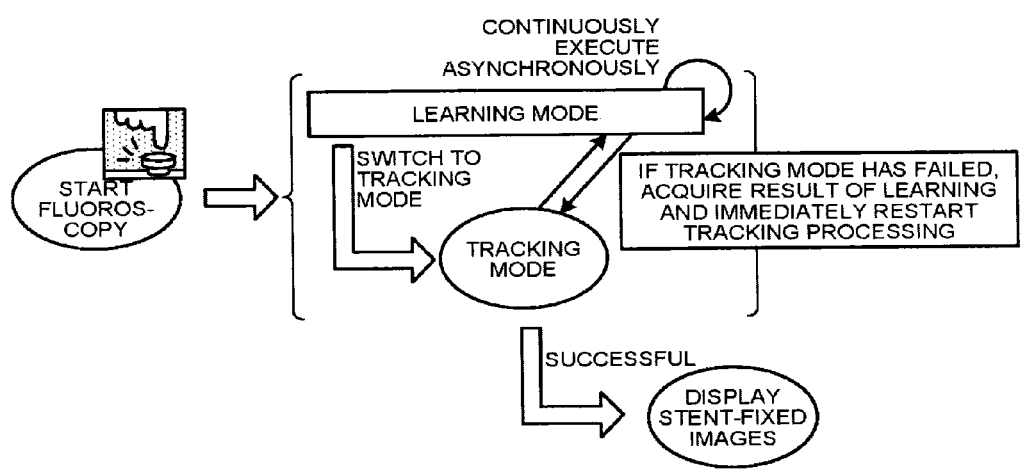
FIG. 15 is a diagram for explaining one example of processing that a detection control unit according to a second embodiment performs.

FIG. 15 is a diagram for explaining one example of processing that the detection control unit 21a according to the second embodiment performs. For example, as illustrated in FIG. 15, once fluoroscopy is stated, the detection control unit 21a controls the marker coordinate detection unit 26a to execute processing of the Learning mode. Here, as illustrated in FIG. 15, in the stent marker detection processing, the detection control unit 21a according to the second embodiment keeps the Learning mode executed in a manner asynchronous with the Tracking mode. More specifically, the marker coordinate detection unit 26a identifies the stent marker by executing the Learning mode by use of a predetermined number of X-ray images, and detects the stent marker from subsequent new X-ray images by use of the identification result. In this identification and detection, the marker coordinate detection unit 26a continuously applies processing of the Learning mode to the new X-ray images, and constantly searches for a region that resembles the stent marker the most within each of the X-ray images.

If the corrected-image generation unit 26b has failed in processing of the Tracking mode, the detection control unit 21a causes execution of detecting the coordinate points of the stent marker in the new X-ray images using a processing result of the Learning mode continuously executed. For example, making a substantial change in the manipulation conditions (the angle of the C-arm 15, the height of the couch, the FOV, and the SID) during fluoroscopy may cause a failure to the Tracking mode. Here, in a conventional X-ray diagnostic apparatus, the Learning mode is executed again when the processing has failed a predetermined number of times. More specifically, a predetermined number of X-ray images are generated even after outputting stent-fixed images has failed, and detection of the stent marker is executed on these X-ray images by use of the processing result of the Learning mode that has been executed for the first time.

When a substantial change has been made in the manipulation conditions, it is difficult to detect the stent marker even by use of a processing result of the Learning mode initially executed. For this reason, in the X-ray diagnostic apparatus 100 according to the second embodiment, the Learning mode is kept executed, so that the stent marker within new X-ray images is detected by use of a processing result of the Learning mode corresponding to several tens of frames starting from a frame where outputting stent-fixed images has failed for the first time. In this manner, a time until recovery from failure can be substantially reduced.

Figure 16:
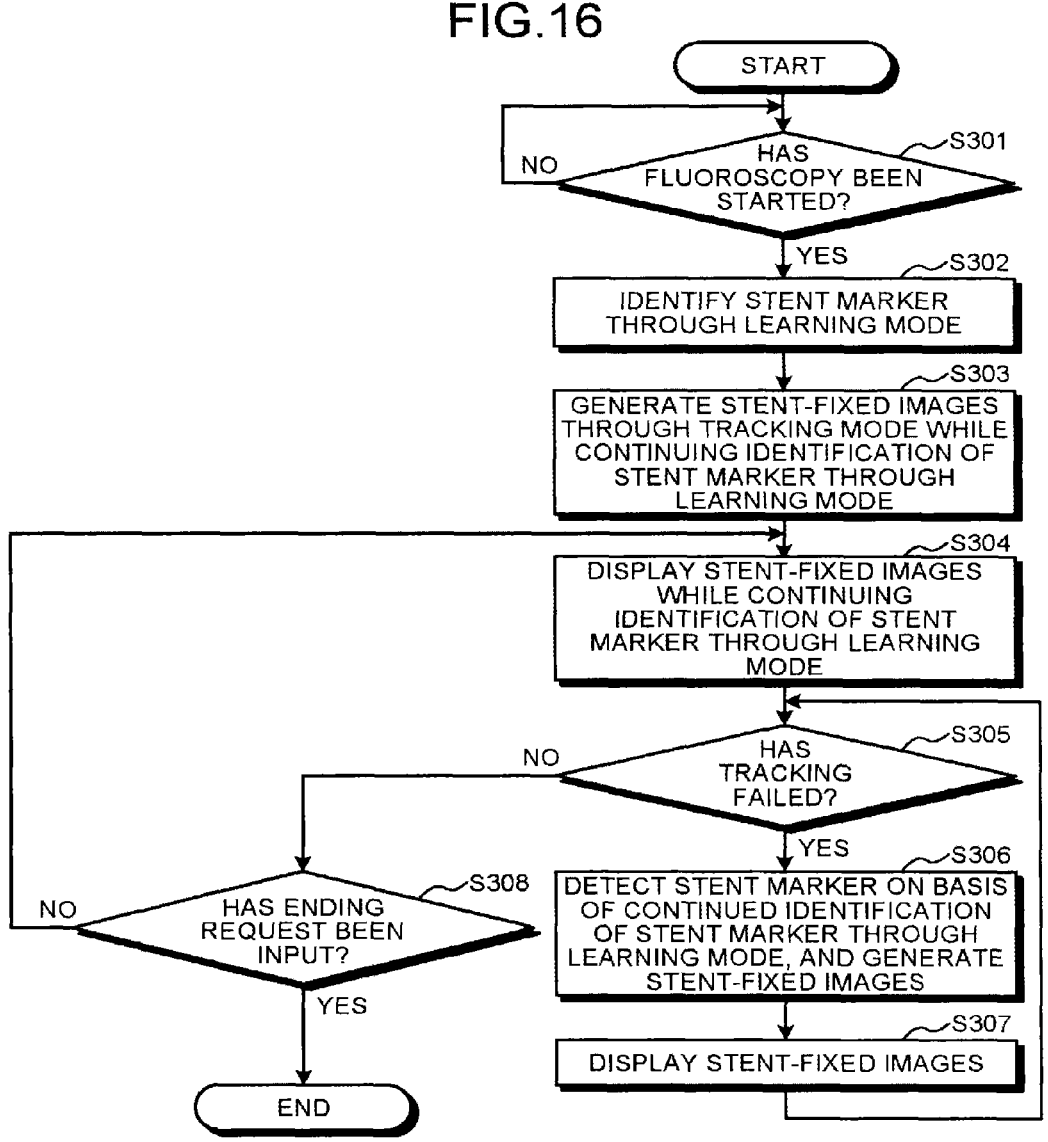
FIG. 16 is a flowchart illustrating a procedure of processing in an X-ray diagnostic apparatus according to the second embodiment.

The following describes, with reference to FIG. 16, a procedure of processing that the X-ray diagnostic apparatus 100 performs. FIG. 16 is a flowchart illustrating a procedure of processing in the X-ray diagnostic apparatus 100 according to the second embodiment. As illustrated in FIG. 16, in the X-ray diagnostic apparatus 100 according to the second embodiment, if fluoroscopy has been started (Yes at Step S301), the marker coordinate detection unit 26a identifies a stent marker (Step S302) through the Learning mode.

The marker coordinate detection unit 26a then detects the stent marker in new X-ray images while keeping identification of the stent marker through the Learning mode, and the corrected-image generation unit 26b generates stent-fixed images through the Tracking mode (Step S303). The display control unit 21b then displays the stent-fixed images on the display unit (Step S304).

Subsequently, when the corrected-image generation unit 26h has failed in Tracking (Yes at Step S305), the detection control unit 21a subjects the stent marker to identification through the Learning mode that has been continuously executed, and performs control so that the stent marker in new X-ray images can be detected based on the identification result, and the corrected-image generation unit 26b generates stent-fixed images (Step S306). The display control unit 21b then displays the generated stent-fixed images on the display unit 23 (Step S307), and the procedure returns to processing at Step S305. By contrast, the corrected-image generation unit 26b has not failed in the Tracking (No at Step S305), the X-ray diagnostic apparatus 100 determines whether the ending request has been input (Step S308). If the ending request has been input (Yes at Step S308), the procedure is ended. By contrast, if the ending request has not been input (No at Step S308), the display control unit 21b displays stent-fixed images (Step S304) while identification of the stent marker through the Learning mode is continued.

As described above, according to the second embodiment, the detection control unit 21a performs control so that, while X-ray images are being generated by the image data generator 24, the marker coordinate detection unit 26a can continue to execute processing of the Learning mode with respect to the stent marker. The detection control unit 21a also performs control so that, when the corrected-image generation unit 26b has failed in generating a corrected image, the position of the stent marker in a newly generated X-ray image can be detected based on a localization result of the localization processing that have continued to be executed. The X-ray diagnostic apparatus 100 according to the second embodiment thus can display a stent-fixed image immediately despite a change in the conditions of manipulation.

Third Embodiment

Described in the above-described second embodiment is a case where, while the Learning mode is kept executed, the Tracking mode, where a predetermined target (a stent marker) detected based on a new processing result of the Learning mode is placed at the same positions, is executed after there is any change in the conditions of manipulation. Described in a third embodiment is a case where, for successful execution of the Tracking mode, detection processing of the predetermined target is modified in accordance with a change in the conditions of manipulation. The third embodiment is different from the first embodiment in specific contents of control that the detection control unit 21a performs. The following description centers on this difference. The following description uses a stent marker as an example of a predetermined target.

Figure 17:
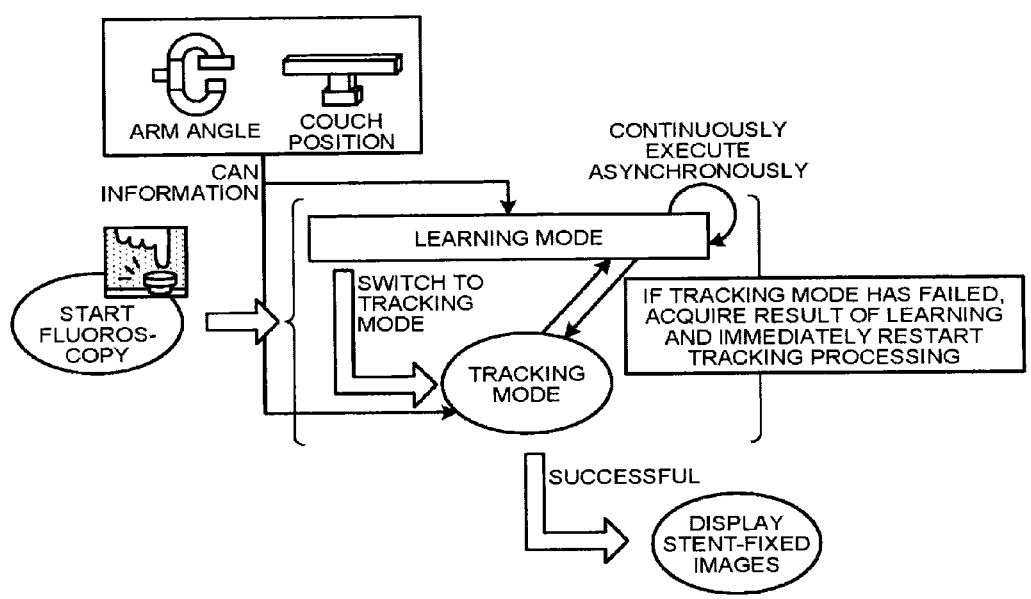
FIG. 17 is a diagram for explaining one example of processing that a detection control unit according to a third embodiment performs.

According to the third embodiment, the detection control unit 21a performs control so that: when any condition of manipulation on a subject is changed, a processing result from the Learning mode can be changed in accordance with a specific change in the conditions of manipulation; and the position of a stent marker contained in a newly generated X-ray image can be detected based on the thus changed processing result. FIG. 17 is a diagram for explaining one example of processing that the detection control unit 21a according to the third embodiment performs. For example, as illustrated in FIG. 17, once fluoroscopy is started, the detection control unit 21a controls the marker coordinate detection unit 26a to execute processing of the Learning mode. Here, as illustrated in FIG. 17, the detection control unit 21a according to the third embodiment acquires controller area network (CAN) information such as the angle of the arm and the position of the couch (table) from the C-arm 15 and the table moving mechanism 18. Here, the CAN information refers to information that is transferred bidirectionally between devices.

The detection control unit 21a then determines based on the acquired CAN information whether there has been any change in the conditions of manipulation. If there has been any change in the conditions of manipulation, the detection control unit 21a changes the detection processing of the stent marker in accordance with a specific change. For example, when the C-arm 15 or the couch (table) has been shifted, the detection control unit 21a calculates a shift amount thereof from the CAN information, and modifies the position of the stent marker identified through the Learning mode. In one illustrative example, the detection control unit 21a shifts, in accordance with the calculated shift amount, a target region (such as the region R1 in FIG. 5) from which to detect the stent marker extracted by the marker coordinate detection unit 26a in the Learning mode. More specifically, shifting of the C-arm 15 or the like causes the target region, from which the stent marker is detected, to also shift by the corresponding amount. In response, the detection control unit 21a shifts the target region, and performs control so that the marker coordinate detection unit 26a can detect the stent marker in a region to which the target region has shifted. In this manner, stent-fixed images can be displayed without having the Learning mode executed even after there is a change in the conditions of manipulation.

Figure 18:
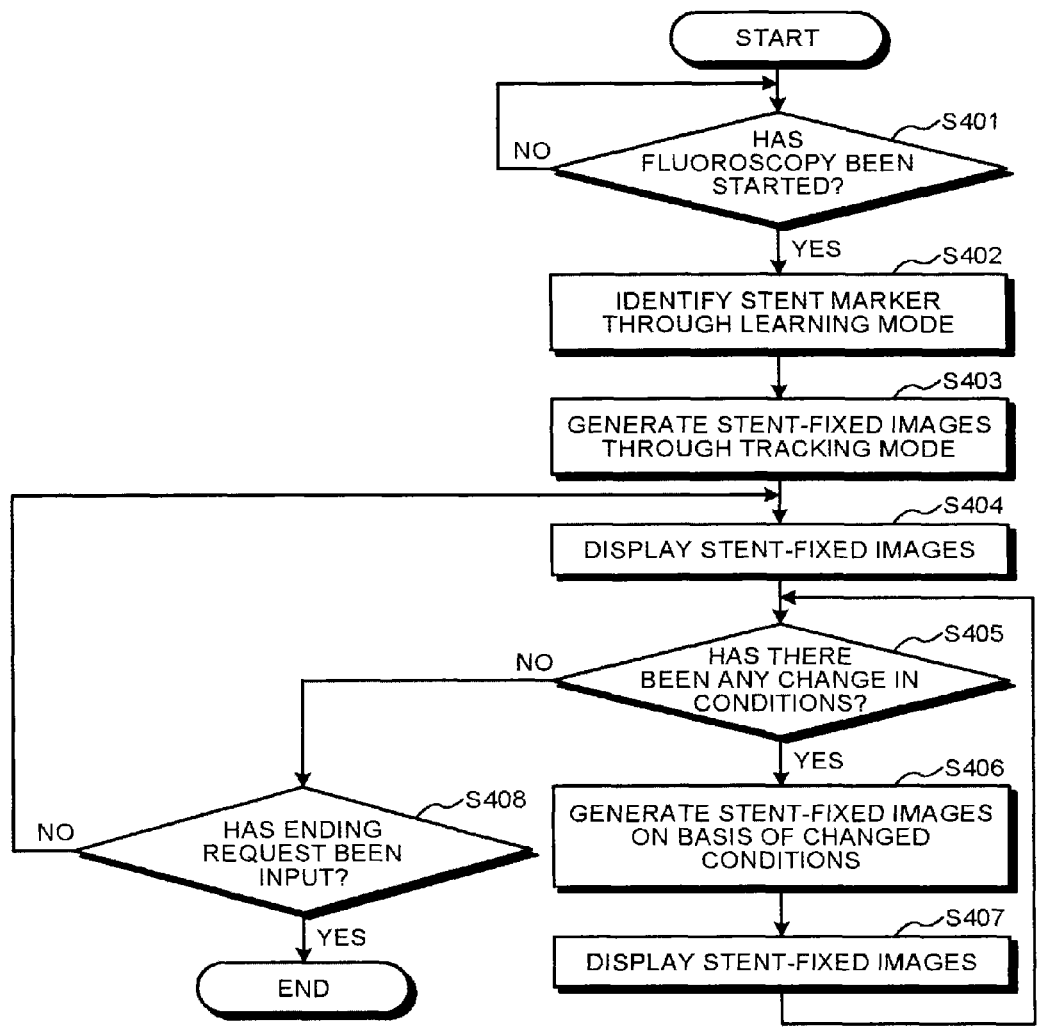
FIG. 18 is a flowchart illustrating a procedure of processing in an X-ray diagnostic apparatus according to the third embodiment.

The following describes, with reference to FIG. 18, a procedure of processing that the X-ray diagnostic apparatus 100 performs. FIG. 18 is a flowchart illustrating a procedure of processing in the X-ray diagnostic apparatus 100 according to the third embodiment. As illustrated in FIG. 18, in the X-ray diagnostic apparatus 100 according to the third embodiment, if fluoroscopy has been started (Yes at Step S401), the marker coordinate detection unit 26a identifies the stent marker through the Learning mode (Step S402).

When the stent marker in new X-ray images is then detected based on the identification result from the marker coordinate detection unit 26a, the corrected-image generation unit 26b generates stent-fixed images through the Tracking mode (Step S403), and the display control unit 21b displays the stent-fixed images on the display unit (Step S404). The detection control unit 21a then determines based on the CAN information whether there has been any change in the conditions (Step S405). If there has been any change in the conditions (Yes at Step S405), the detection control unit 21a changes a processing result of the Learning mode, based on any condition that has been changed. The corrected-image generation unit 26b generates stent-fixed images based on the changed condition (Step S406). The display control unit 21b then displays the generated stent-fixed images on the display unit 23 (Step S407), and the procedure returns to processing at Step S405. By contrast, if there has been no change in the conditions (No at Step S405), the X-ray diagnostic apparatus 100 determines whether the ending request has been input (Step S408). If the request has been input (Yes at Step S408), the processing is ended. By contrast, if the ending request has not been input (No at Step S408), the display control unit 21b continues to display stent-fixed images (Step S404).

As described above, according to the third embodiment, when there has been a change in the conditions of manipulation on a subject, the detection control unit 21a changes a processing result of the Learning mode in accordance with any specific change in the conditions, and performs control so that the positions of the stent marker contained in X-ray images newly generated based on the changed processing result can be detected. The X-ray diagnostic apparatus 100 according to the third embodiment can reduce a processing time despite a change in the conditions of manipulation.

Fourth Embodiment

The above-described embodiments describe cases where a single stent is used. In endovascular intervention treatment, however, a plurality of stents may be inserted at the same time. For example, when two stents are inserted, the X-ray diagnostic apparatus 100 according to a fourth embodiment, the system controller 21 performs control described below, based on the distance between these two stents. The distance between the stents may be calculated by the marker coordinate detection unit 26a by use of coordinate points designated via the input unit 22 by an operator (doctor) referring to the first frame (an original image). Alternatively, the distance therebetween may be calculated by use of the coordinate points of stent markers that have been detected by the marker coordinate detection unit 26a by use of a teacher image from within the first frame.

Figure 19A:
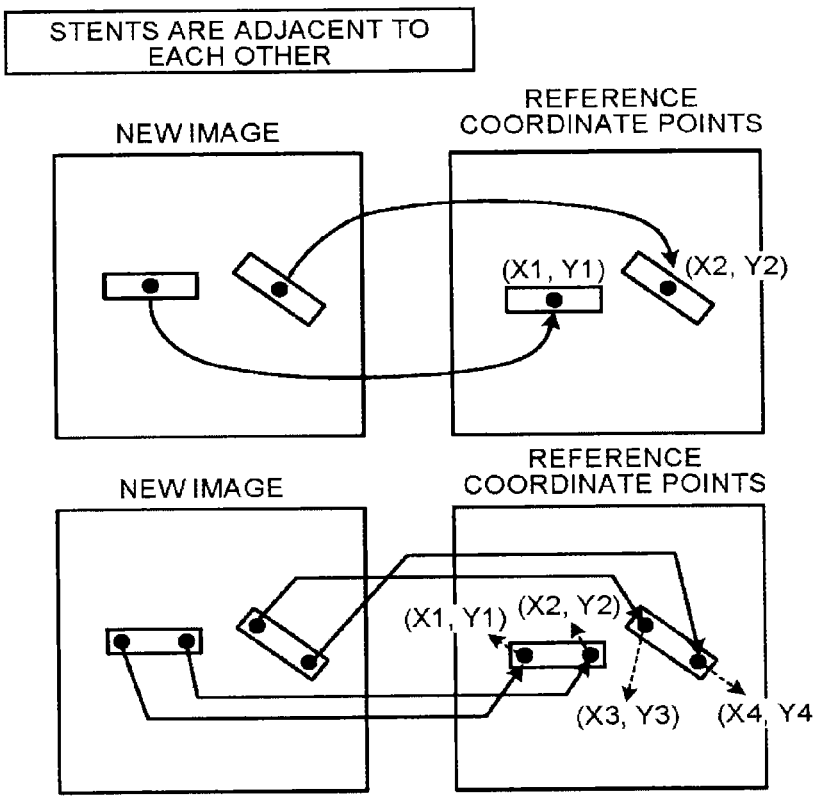
FIGS. 19A and 19B are diagrams for explaining an X-ray diagnostic apparatus according to a fourth embodiment.
Figure 19B:
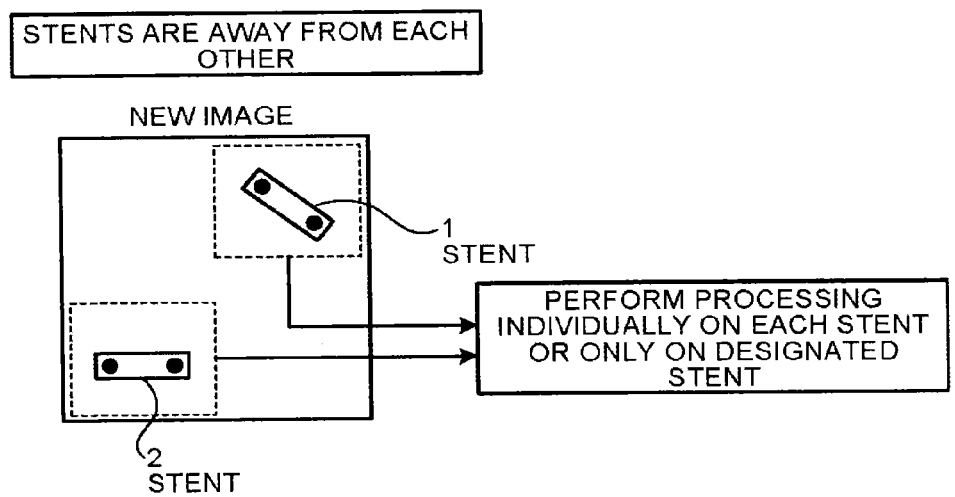

Specifically, if the two stents are determined to be adjacent to each other because the distance therebetween is not larger than a predetermined distance (for example, not more than 50 mm) on a plane space, the system controller 21 controls the corrected-image generation unit 26b to generate corrected images through image deformation such that a plurality of the coordinate points of the stent markers associated with the respective stents are placed at the same positions as a plurality of reference positions that correspond to the stent markers. FIGS. 19A and 19B are diagrams for explaining an X-ray diagnostic apparatus according to the fourth embodiment. For example, with stents each having one stent marker at the central part of a balloon, the corrected-image generation unit 26b performs image deformation under the control of the system controller 21 such that, as illustrated in the upper part of FIG. 19A, the coordinate points of two stent markers detected in each new image coincide with the reference coordinate points (X1,Y1) and (X2,Y2) for the two respective stents.

For example, with stents each having two stent markers at opposite sides of a balloon, the corrected-image generation unit 26b performs image deformation under the control of the system controller 21 such that, as illustrated in the lower part of FIG. 19A, the coordinate points of four stent markers detected in each new image coincide with the reference coordinate points (X1,Y1) and (X2,Y2), and (X3,Y3) and (X4,Y4), for the two respective stents.

By contrast, if the two stents are determined to be away from each other because the distance therebetween is larger than a predetermined distance (for example, more than 50 mm) on a plane in the actual space, excessive image deformation needs to be performed in order that positions of the two respective stents coincide with corresponding positions on one image. To eliminate the need to perform excessive image deformation, as illustrated in FIG. 19B, the system controller 21 controls the image processor 26 to separately perform processing on the two respective stents (a stent 1 and a stent 2) when the two stents are away from each other. For example, the system controller 21 controls the image processor 26 to generate images to be displayed of two kinds in order that a moving image display of stent-fixed images in which the positions of the stent 1 coincide with each other, and a moving image display of stent-fixed images in which the positions of the stent 2 coincide with each other are executed on two child windows on the monitor.

Alternatively, the system controller 21 controls the image processor 26 to display a region-of-interest designation screen to be used for designating one of the two stents as a region of interest. After any one of the stents is designated as the region of interest via the input unit 22, the system controller 21 controls the image processor 26 to perform processing only on the designated stent, as illustrated in FIG. 19B. For example, the system controller 21 controls the image processor 26 to generate only stent-fixed images in which the positions of the thus designated stent 1 coincide with each other. Therefore, even when medical treatment is being performed with a plurality of stents, the most appropriate stent-fixed images can be displayed as moving images in accordance with the distance between the stents. As described above, when a plurality of stents are used, the X-ray diagnostic apparatus 100 performs, with respect to each stent, the above-described control over the Learning mode.

Fifth Embodiment

Figure 20:
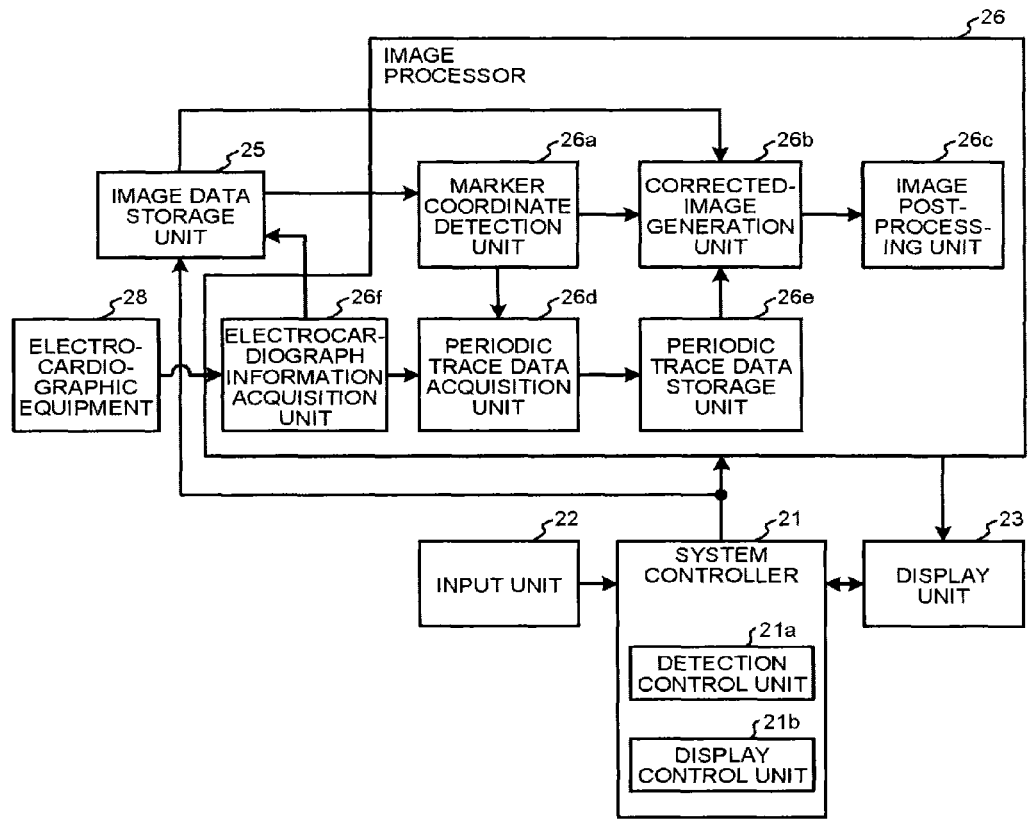
FIG. 20 is a diagram illustrating one example of the configuration of an image processor according to a fifth embodiment.

Described in the above-described embodiments are cases where a coordinate point of a stent marker is detected with respect to each new image for generation of corrected images. In a case described in a fifth embodiment, a coordinate point of a stent marker is not detected with respect to a new image for generation of a corrected image. FIG. 20 is a diagram illustrating one example of the configuration of the image processor 26 according to the fifth embodiment. The image processor 26 according to the fifth embodiment is different from the image processor 26 illustrated in FIG. 3 in further including an electrocardiograph information acquisition unit 26f, a periodic trace data acquisition unit 26d, and a periodic trace data storage unit 26e. The following description centers on this difference.

Figure 21:
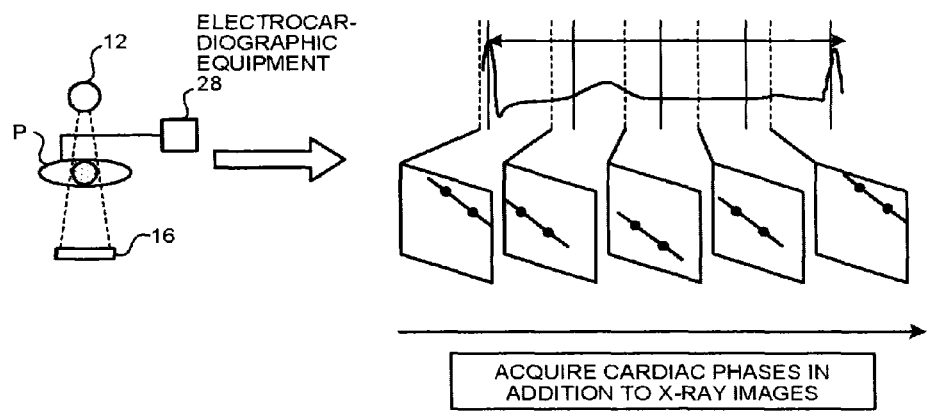
FIG. 21 is a diagram for explaining X-ray images according to the fifth embodiment.

Here, in the fifth embodiment, as illustrated in FIG. 20, electrocardiographic equipment 28 that acquires an electrocardiographic waveform is attached to a subject P. The electrocardiograph information acquisition unit 26f then acquires, from the electrocardiographic equipment 28, the electrocardiographic waveform of the subject P having a stent inserted therein. The electrocardiograph information acquisition unit 26f can transfer an electrocardiographic waveform acquired from the electrocardiographic equipment 28 to each of the image data storage unit 25 and the periodic trace data acquisition unit 26d. More specifically, as illustrated in FIG. 21, the X-ray diagnostic apparatus 100 according to the fifth embodiment generates X-ray images in a time-series manner with the X-ray tube 12 emitting X-rays and with the X-ray detector 16 detecting X-rays transmitted through the subject, as in the cases of the above-described embodiments, and, additionally, acquires cardiac phases of the subject P at the times of generation of X-ray images with the electrocardiograph information acquisition unit 26f acquiring an electrocardiographic waveform from the electrocardiographic equipment 28 attached to the subject P. FIG. 21 is a diagram for explaining X-ray images according to the fifth embodiment.

Here, the X-ray diagnostic apparatus 100 in the fifth embodiment performs preliminary radiography for a predetermined period (for example, the duration of three heartbeats) starting from when display processing for images to be displayed is started. With this radiography, the image data storage unit 25 stores therein X-ray images corresponding to the duration of three heartbeats with cardiac phase information appended thereto, as preliminary images. A preliminary image refers to an image for collecting periodic trace data described later, and an image for use in diagnosis may be used as the preliminary image. Furthermore, an image obtained prior to the current radiography may be used as a preliminary image.

Figure 22A:
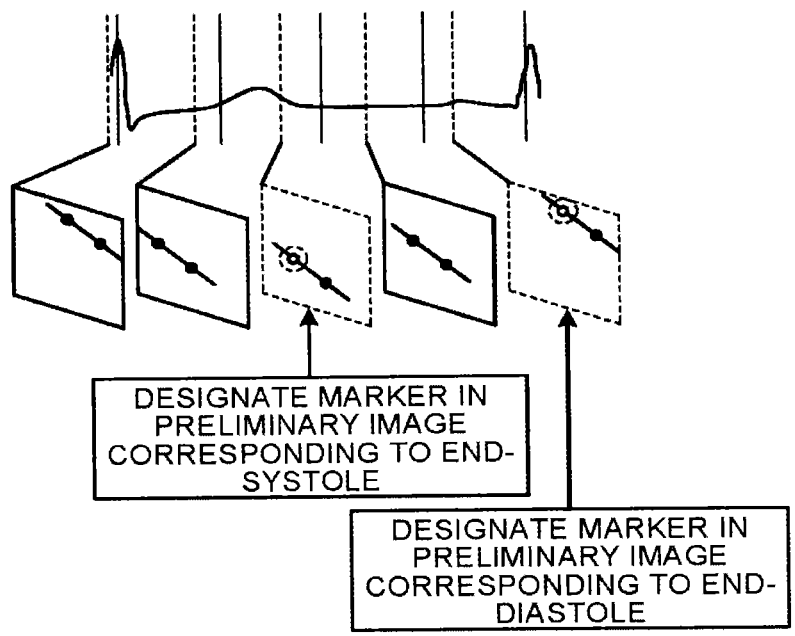
FIGS. 22A and 22B are diagrams for explaining a marker coordinate detection unit according to the fifth embodiment.
Figure 22B:
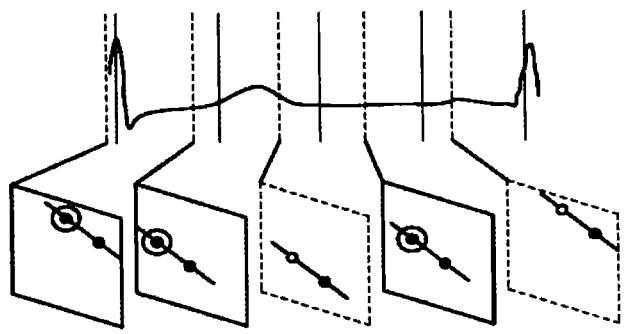

The marker coordinate detection unit 26a according to the fifth embodiment then acquires a coordinate point of a stent marker with respect to each of the preliminary images. Next described with reference to FIGS. 22A and 22B are one example of processing that the marker coordinate detection unit 26a according to the fifth embodiment performs on the preliminary images to detect the coordinate point of the stent marker. FIGS. 22A and 22B are diagram for explaining the marker coordinate detection unit according to the fifth embodiment. First of all, when the preliminary images are stored in the image data storage unit 25, the system controller 21 performs control so that, for example, a plurality of preliminary images in a time-series manner that correspond to the duration of one heartbeat can be displayed on the monitor of the display unit 23. When these preliminary images are displayed, as illustrated in FIG. 22A, the system controller 21 performs control so that an operator can see what position (cardiac phase) in the electrocardiographic waveform each of the preliminary images has been generated at.

As illustrated in FIG. 22A, the operator then designates one position of a marker in, for example, one preliminary image corresponding to the end-systole, and further designates one position of the corresponding marker in another preliminary image corresponding to the end-diastole, from among the preliminary images displayed on the monitor. The following description assumes that, while a preliminary image at the timing of 30% in the interval between R waves (30% in the R-R interval) is designated as the preliminary image corresponding to the end-systole, a preliminary image at the timing of 70% in the interval between R waves (70% in the R-R interval) is designated as the preliminary image corresponding to the end-diastole.

The marker coordinate detection unit 26a detects the coordinate points of the stent markers designated in the above-described two preliminary images, and defines rectangles centering on the coordinate points of the respective designated stent markers. As illustrated in FIG. 22B, the marker coordinate detection unit 26a then extracts from the other preliminary images, for example, by use of a cross-correlation method, patterns that resemble patterns in the defined rectangles, and detects a coordinate point having the highest cross-correlation value as the coordinate point of the stent marker.

After the marker coordinate detection unit 26a completes the processing, the system controller 21 may perform control so that a result of the processing performed on the preliminary images by the marker coordinate detection unit 26a can be displayed on the monitor, to allow an operator to modify the coordinate points of the stent markers via a mouse of the input unit 22. As described in connection with the above-described embodiments, the marker coordinate detection unit 26a may execute the processing by use of a teacher image also in this embodiment. Furthermore, the processing for detecting the coordinate points of the markers may be repeatedly executed on respective pluralities of preliminary images where each plurality of preliminary images correspond to one heartbeat, or may be executed on a plurality of preliminary images corresponding to three heartbeats at one time.

Figure 23A:
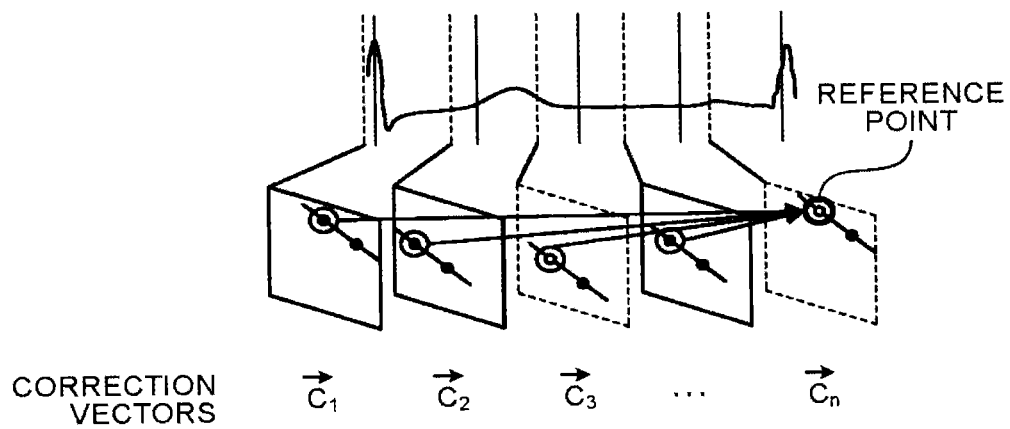
FIGS. 23A and 23B are diagrams for explaining a periodic trace data acquisition unit.

The periodic trace data acquisition unit 26d then acquires periodic trace data of the stent marker in a time-series manner, based on: coordinate points of the stent marker detected in each plurality of preliminary images by the marker coordinate detection unit 26a; and respective cardiac phases of the preliminary images at the times of generation of the preliminary images. Here, suppose that the operator selects, as a reference point, the coordinate point of the stent marker in the "preliminary image at 70% in the R-R interval" out of the two preliminary images in which the stent marker has been designated. In this case, as illustrated in FIG. 23A, the periodic trace data acquisition unit 26d calculates, as a correction vector, the difference between a coordinate point of the stent marker detected in each of the preliminary images by the marker coordinate detection unit 26a and the reference point in the "preliminary image at 70% in the R-R interval".

Figure 23B:
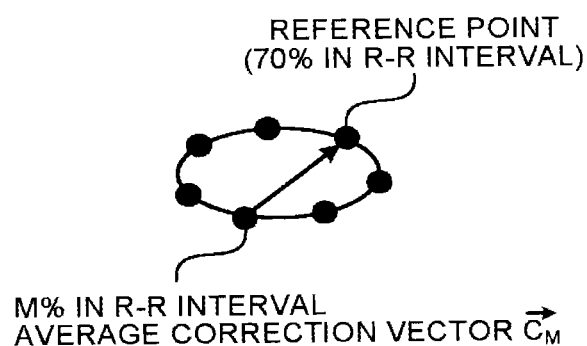

Subsequently, the periodic trace data acquisition unit 26d calculates an average correction vector with respect to each cardiac phase from correction vectors calculated for all of the preliminary images corresponding to the three heartbeats. For example, as illustrated in FIG. 23B, the periodic trace data acquisition unit 26d calculates an average correction vector (vector CM) at the "cardiac phase: M % in R-R interval" with respect to the reference point at the "cardiac phase: 70% in R-R interval", thereby generating periodic trace data in which the cardiac phases are associated with the average correction vectors.

Back to FIG. 20, the periodic trace data storage unit 26e stores therein the periodic trace data generated by the periodic trace data acquisition unit 26d. This embodiment illustrates a case where the marker coordinate detection unit 26a detects coordinate points only of the upper stent marker in the preliminary images, as illustrated in FIGS. 22A and 22B. However, the embodiment is not limited to this case, and the marker coordinate detection unit 26a may detect coordinate points only of the lower stent marker in the preliminary images, or the marker coordinate detection unit 26a may detect coordinate points of both of the stent markers.

Figure 24:
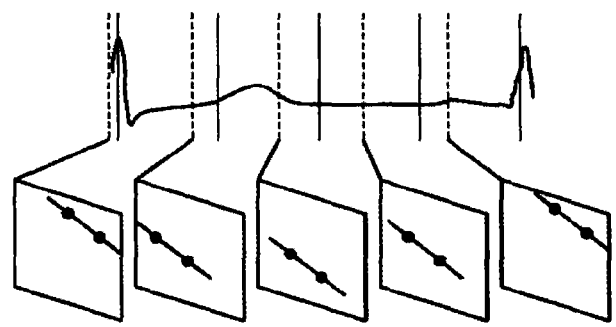
FIG. 24 is a diagram for explaining new images according to the fifth embodiment.

When the periodic trace data is stored into the periodic trace data storage unit 26e, the X-ray diagnostic apparatus 100 executes radiography/fluoroscopy of new images to be subjected to image processing, in accordance with an instruction of an operator. In this manner, as illustrated in FIG. 24, the image data storage unit 25 sequentially stores therein the new images to be subjected to image processing in association with cardiac phases estimated from an electrocardiographic waveform. FIG. 24 is a diagram for explaining new images in the fifth embodiment.

Figure 25:
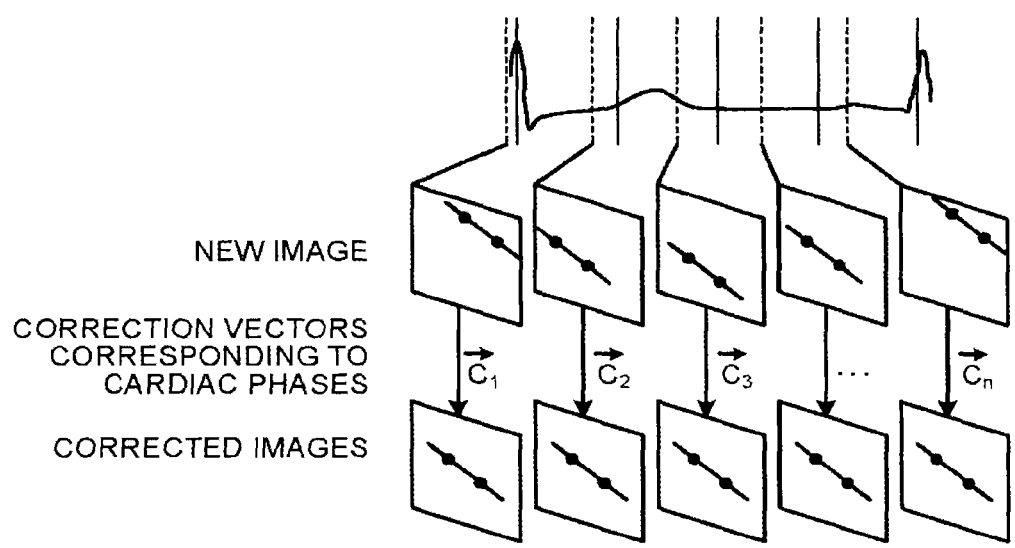
FIG. 25 is a diagram for explaining a corrected-image generation unit according to the fifth embodiment.

Back to FIG. 20, each time a new image is generated in a time-series manner, the corrected-image generation unit 26b according to the fifth embodiment generates a corrected image from the new image, based on the periodic trace data stored in the periodic trace data storage unit 26e and a cardiac phase at the time of generation of the new image. More specifically, as illustrated in FIG. 25, once a new image is stored, the corrected-image generation unit 26b acquires from the periodic trace data an average correction vector corresponding to a cardiac phase at the time of generation of the new image, and generates a corrected image by using the acquired average correction vector.

As described above, in the fifth embodiment, corrected images and images to be displayed are generated from sequentially generated new images without the use of the marker coordinate detection unit 26a. Therefore, this embodiment reduces a processing load on the image processor 26 to allow a reduction in processing time, thereby enabling more immediate display, of X-ray images as moving images with the visibility of a stent ensured.

Sixth Embodiment

Figure 26:
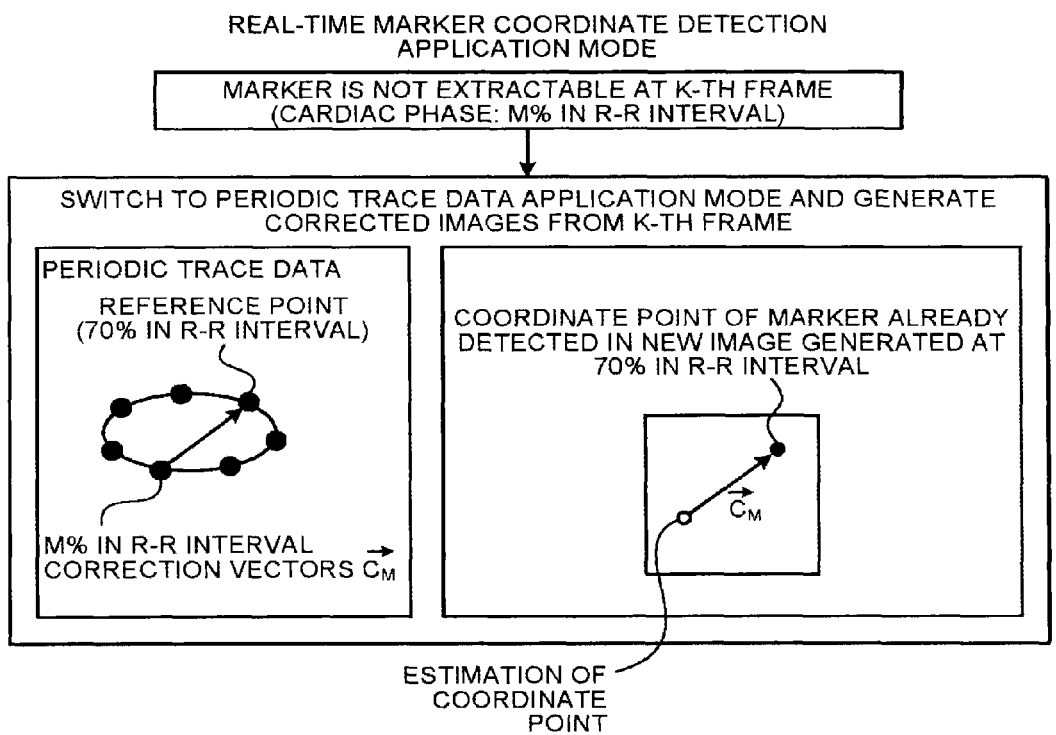
FIG. 26 is a diagram for explaining an X-ray diagnostic apparatus according to a sixth embodiment.
Figure 27:
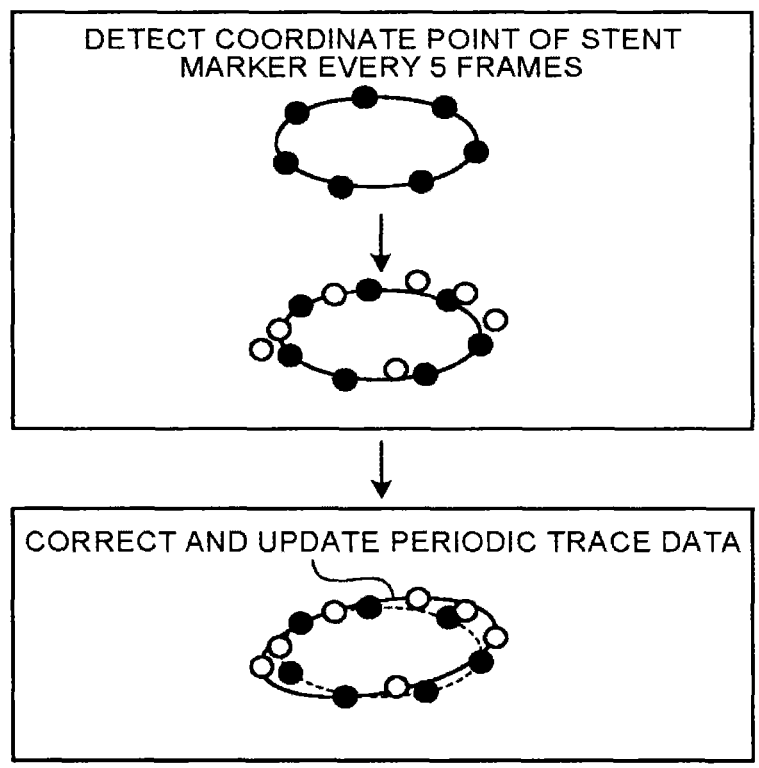
FIG. 27 is a diagram for explaining the X-ray diagnostic apparatus according to the sixth embodiment.

A sixth embodiment describes, with reference to FIG. 26 and FIG. 27, a case where functions of the X-ray diagnostic apparatuses 100 according to the respective above-described embodiments are used in combination. FIG. 26 and FIG. 27 are diagrams for explaining the X-ray diagnostic apparatus 100 according to the sixth embodiment. The X-ray diagnostic apparatus 100 according to the sixth embodiment accepts, from an operator via the input unit 22, an instruction to execute either of the following modes explained in the above-described embodiments: the "real-time marker coordinate detection application mode" where processing for generating corrected images is executed by use of coordinate points of a stent marker detected in new images by the marker coordinate detection unit 26a; and the "periodic trace data application mode" where processing for generating corrected images is executed by use of periodic trace data.

Here, when the marker coordinate detection unit 26a has failed to extract a stent marker from a new image while the "real-time marker coordinate detection application mode" is running, the system controller 21 according to the sixth embodiment controls the corrected-image generation unit 26b to generate corrected images after switching to the "periodic trace data application mode". For example, as illustrated in FIG. 26, when a stent marker is not extractable at the k-th frame (cardiac phase: M % in the R-R interval), the corrected-image generation unit 26b acquires a "vector CM" from the periodic trace data under the control of the system controller 21. The "vector CM" is a correction vector of the "cardiac phase at M % in the R-R interval" with respect to the reference point (at 70% in the R-R interval).

As illustrated in FIG. 26, while the "real-time marker coordinate detection application mode" is executed, the corrected-image generation unit 26b then, from a coordinate point of the stent marker already detected by the marker coordinate detection unit 26a from a new image generated at 70% in the R-R interval, estimates a coordinate point of the stent marker at the k-th frame by using the "vector CM" as a correction vector to generate a corrected image.

On the other hand, also while the "periodic trace data application mode" is running, the system controller 21 according to the sixth embodiment performs control, using functions of the marker coordinate detection unit 26a under the "real-time marker coordinate detection application mode", so that the periodic trace data can be modified and updated. For example, as illustrated in FIG. 27, under the control of the system controller 21, the marker coordinate detection unit 26a detects respective coordinate points of the stent marker from selected images, which have been selected from sequentially generated new images in such a manner that one frame is selected at every predetermined interval (for example, every five frames).

As illustrated in FIG. 27, under the control of the system controller 21, the periodic trace data acquisition unit 26d then modifies and updates periodic trace data, which is stored in the periodic trace data storage unit 26e, based on: respective coordinate points of the stent marker detected in selected images by the marker coordinate detection unit 26a; and respective cardiac phases of the selected images at times of generation of the selected images. For example, under the control of the system controller 21, the periodic trace data acquisition unit 26d modifies and updates the periodic trace data every 100 milliseconds. Subsequently, under the control of the system controller 21, the corrected-image generation unit 26b executes processing for generating corrected images by using the updated periodic trace data stored in the periodic trace data storage unit 26e.

As described above, in the sixth embodiment, corrected images can be generated by use of the periodic trace data when extraction of a coordinate point of a stent marker has failed, for example, because of image quality degradation of a new image while the "real-time marker coordinate detection application mode" is executed. The sixth embodiment thus makes it possible to continuously display X-ray images with a high visibility of a stent as moving images. Furthermore, in the sixth embodiment, the periodic trace data can be modified and updated by use of a detected coordinate point of a marker while the "periodic trace data application mode" is running. The sixth embodiment thus enables highly instantaneous image display, thereby making it possible to more reliably ensure the visibility of a stent in displayed X-ray images.

Note that whether to execute "the function of displaying as moving images X-ray images in which a stent appears stationary (hereinafter referred to as the present function)" explained in the above-described embodiments may be determined by an operator of the X-ray diagnostic apparatus 100 (a doctor or a technician). More specifically, with a button to select ON/OFF of the present function provided to the input unit 22 or near the couch, X-ray images in which a stent appears stationary can be displayed as moving images only when a doctor who performs treatment desires to display such X-ray images.

While the present function is in operation, a stent displayed on the monitor appears almost stationary. It is thus not needed to perform X-ray irradiation at a high rate in radiography/fluoroscopy that is executed while the present function is in operation. Therefore, the system controller 21 may perform the following control processing. More specifically, when the operation of the present function is started, the system controller 21 reduces an irradiation rate (for example, a pulse rate or a frame rate) for X-rays emitted from the X-ray tube 12, and returns the irradiation rate for X-rays to the original rate after operation of the present function is ended. For example, in cases of treatment of coronary arteries of the heart, the frame rate is normally about 15 to 30 frames/sec, and is reduced to, for example, half when the present function is in operation. The system controller 21 increases or decreases the irradiation rate for X-rays in accordance with a result of detection of a stent marker from the rate at the time when operation of the present function is started. Specifically, the system controller 21 increases again the irradiation rate for X-rays when detection of the stent marker has successively failed a predetermined number of times. In contrast, the system controller 21 further decreases the irradiation rate for X-rays when detection of the stent marker has been successful a predetermined number of times. This processing enables reduction in X-ray exposure.

Furthermore, for a stent having two stent markers attached thereto, processing described below may be additionally included at the time of generation of corrected images. More specifically, the corrected-image generation unit 26b further correct corrected images by rotation based on positional information of the two stent markers so that the orientation of the stent visualized in the corrected images can be horizontal or vertical. This correction allows a doctor to more easily recognize, for example, the state of stent expansion because the doctor can view images that have the stent kept oriented horizontally or vertically.

In general, when performing endovascular intervention treatment, a doctor intermittently performs radiography/fluoroscopy. For example, a doctor performs radiography/fluoroscopy for 30 seconds, then stops radiography/fluoroscopy, and then restarts radiography/fluoroscopy 30 seconds later. Here, suppose that the radiography/fluoroscopy performed for the first 30-second period and the radiography/fluoroscopy performed subsequently are denoted as "A" and "B", respectively, and "A" and "B" are performed independently and without correlation with each other. In such a case, it is highly likely that the angle of a stent appearing in stent-fixed images displayed during the radiography/fluoroscopy "A" is different from the angle (inclination) of a stent appearing in stent-fixed images displayed during the radiography/fluoroscopy "B". For this reason, the stent is not clearly visible to a doctor when the doctor sees images displayed while the radiography/fluoroscopy "B" is running.

For this reason, on condition that "A" and "B." are performed at an interval within a predetermined time (for example, one minute), the corrected-image generation unit 26b uses, during processing of "B", information acquired during processing of "A" to perform processing for generating corrected images so that the angles of the displayed stents can be the same. Specifically, the corrected-image generation unit 26b performs image deformation of X-ray images generated during the radiography/fluoroscopy "B" so that a stent marker therein may be positioned at a coordinate point of a stent marker extracted from X-ray images generated during the radiography/fluoroscopy "A". With this image deformation, for example, when radiography/fluoroscopy is restarted within one minute, a doctor can observe a stent at the same angle (same inclination), and can continue manipulation without feeling odd. Note that this function is configured to be ON/OFF switchable and to enable a user to set the predetermined time (for example, one minute).

The above-described embodiments explain cases where image deformation is performed so that the positions of two stent markers in newly generated X-ray images can be set at the same positions as those of the two stent markers in an X-ray image at the first frame. However, the embodiments are not limited to this case, and may be a case where corrected images are generated by use of one point depending on two stent markers. More specifically, the marker coordinate detection unit 26a performs processing of the Learning mode on one point depending on the two stent markers (for example, the midpoint between the two stent markers) to identify a position (a coordinate point), and detect, based on a result of the processing, one point depending on the stent markers in new images. The corrected-image generation unit 26b generates corrected images, which have been corrected so that the one point depending on the stent markers that have been detected in each of the corrected images is set at the same point.

In such a case, the corrected-image generation unit 26b uses one point and an angle determined from a feature pattern detected from an X-ray image (for example, the first frame) defined as a reference image. Based on feature patterns detected from target images, which are X-ray images to be corrected, a single predetermined point, and a predetermined angle, the corrected-image generation unit 26b then generates corrected images from the target images. The system controller 21 then displays on the display unit 22, as moving images, corrected images sequentially generated by the corrected-image generation unit 26b.

The following describes a case where a stent, which is a treatment tool, has two feature points (for example, two stent markers). In such a case, the marker coordinate detection unit. 26a detects, as the feature patterns, two feature points belonging to the tool. The corrected-image generation unit 26b then uses, as the single predetermined point, one point determined depending on positions of the two feature points detected from the reference image. The corrected-image generation unit 26b further uses, as the predetermined angle, an angle formed between a line segment connecting the two feature points detected from the reference image and a reference line in the reference image. FIG. 28 to FIG. 31 are diagrams for explaining the image processor 26 according to the sixth embodiment.

Figure 28:
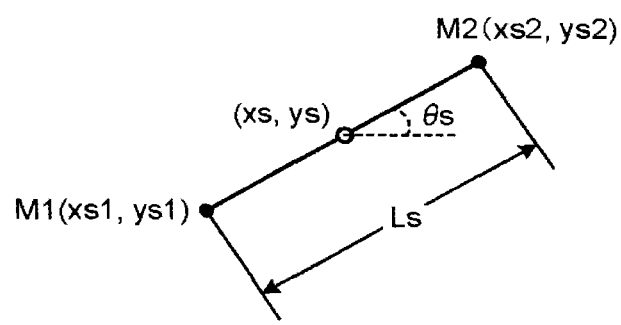
FIG. 28 is a diagram for explaining the image processor according to the sixth embodiment.

For example, the marker coordinate detection unit 26a detects the two markers (M1 and M2) and positions (coordinate points) thereof from the X-ray image at the first frame, which has been defined as the reference image. For example, as illustrated in FIG. 28, the marker coordinate detection unit 26a detects "(xs1,ys1) and (xs2,ys2)" as the positions of M1 and M2. Using the detection result from the marker coordinate detection unit 26a, the corrected-image generation unit 26b determines "one position (coordinate point)" for use in image deformation. For example, as illustrated in FIG. 28, the corrected-image generation unit 26b calculates a central coordinate point "(xs,ys)" between M1 and M2. The central coordinate point is a midpoint of the line segment (hereinafter, the line segment M1 &2) connecting M1 and M2. More specifically, "xs" is "(xs1+xs2)/2" and "ys" is "(ys1+ys2)/2". Furthermore, for example, as illustrated in FIG. 28, the corrected-image generation unit 26b calculates the angle "θs" formed between the line segment M1&2 and the reference line extending in the horizontal direction in the reference image.

Figure 29:
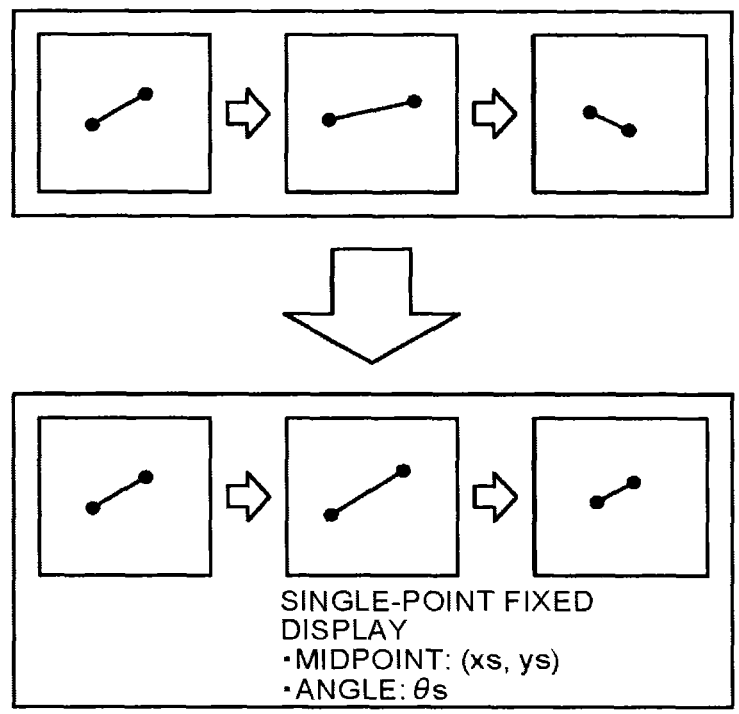
FIG. 29 is a diagram for explaining the image processor according to the sixth embodiment.

Note that "(xs,ys)" and "θs" may be calculated by the system controller 21. An X-ray image to be used as the reference image may be an X-ray image at a frame other than the first frame (for example, the fifth frame). Otherwise, an X-ray image to be used as the reference image may be, for example, a first X-ray image since a cross-correlation value has become larger than a predetermined threshold. In the above-described manner, "the single point and the angle" to be used for image deformation processing are determined, and thereafter, the marker coordinate detection unit 26a detects positions (coordinate points) of M1 and M2 in X-ray images to be corrected (target images) that have been generated after the reference image. Thereafter, as illustrated in FIG. 29, the corrected-image generation unit 26b performs image deformation on the target images so that positions (coordinate points) of the midpoint of the line segment M1&2 in each of the target images can be (xs,ys) and that the angle between the line segment M1&2 and the reference line can be "θs".

More specifically, in the sixth embodiment, image deformation is performed on target images so that a device visualized in corrected images can pass through a single point and that the device visualized in the corrected images can take the same angle (same inclination). The display control unit 21b displays on the display unit 23, as moving images, corrected images sequentially generated by the corrected-image generation unit 26b. In other words, display of moving images in the sixth embodiment is "single-point fixed display", as illustrated in FIG. 29. The single-point fixed display is provided with enhanced visibility of a device as in the case of conventional two-point fixed display because the device is visualized at the substantially same point and at the same inclination.

Figure 30:
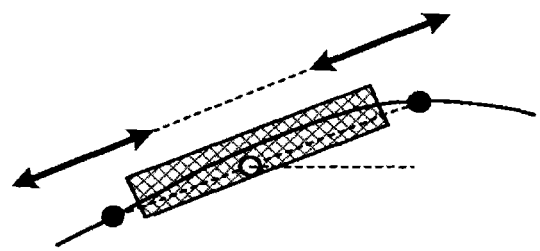
FIG. 30 is a diagram for explaining the image processor according to the sixth embodiment.

However, in the single-point fixed display, while the orientation of a device and the direction of X-ray irradiation (a direction of X-ray radiography) is in a "diagonal relation", when the degree of the "diagonal relation" changes, the distance ("Ls" in FIG. 28) between markers in the reference image fluctuate from one corrected image to another. More specifically, in the single-point fixed display, the distance between two markers may stretch and shorten centering on the white circle, which represents the central coordinate point (xs,ys), as illustrated in FIG. 30. In other words, in the single-point fixed display, not only the visibility of a device can be ensured, but also occurrence of "Foreshortening (a phenomenon where the length of a device appears shorter)" can be recognized. Specifically, the single-point fixed display enables recognition of occurrence of "Foreshortening in a state where the "diagonal relation" is being changed.

Figure 31:
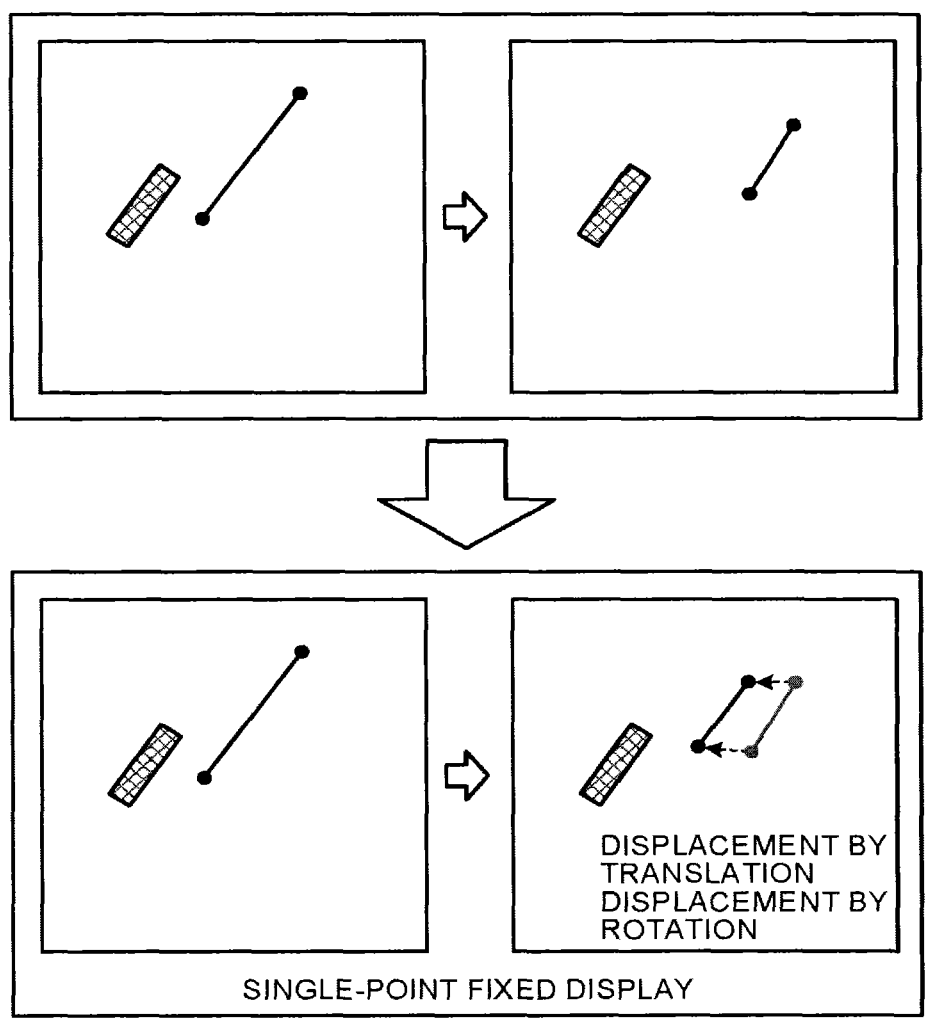
FIG. 31 is a diagram for explaining the image processor according to the sixth embodiment.

Additionally, as illustrated in FIG. 31, image deformation performed in the single-point fixed display is displacement processing that is either of translational displacement and rotational displacement, the sizes of objects located around the device do not change before and after the image deformation. In the single-point fixed display, therefore, even when body tissue around a device is used as an anatomical landmark during medical treatment, a doctor can easily determine a position of the device.

The above describes a case where the single point used for the single-point fixed display is the midpoint of the line segment M1&2 in the reference image. However, the single point used for the single-point fixed display may be M1 or M2 in the reference image. In such a case, for example, the corrected-image generation unit 26b performs image deformation so that a position of M1 (or M2) detected from target images can be the same as the position of M1 (or M2) in the reference image.

Alternatively, the corrected-image generation unit 26b may use a predefined point as the single point used for the single-point fixed display. For example, the corrected-image generation unit 26b may use, as the single point used for the single-point fixed display, the central coordinate point of a region in which corrected images are displayed. In such a case, for example, the corrected-image generation unit 26b performs image deformation so that positions of M1 detected in target images, positions of M2 detected in target images, or positions of the midpoint of the line segment M1&2 in target images can be located at the central coordinate point of a region in which corrected images are displayed. Conditions for setting the single point used in the above-described single-point fixed display may be changed to those desired by an operator of the X-ray diagnostic apparatus.

Furthermore, the above-described information for the Learning mode regarding each set of the conditions of manipulation may be stored each time a content of the conditions of manipulation is changed during manipulation on a subject, and results of the Learning mode may be updated as appropriate. FIG. 32 is a diagram for explaining one example of information for the Learning mode. For example, as illustrated in FIG. 32, a "result of the Learning mode" is stored in the image data storage unit 25 or the storage unit (not illustrated) in association with each "set of the conditions". More specifically, the marker coordinate detection unit 26a executes the Learning mode each time the conditions of manipulation have been changed, and stores a result of the Learning mode into the image data storage unit 25 or the storage unit (not illustrated) in association with the changed conditions of manipulation.

Here, the conditions include, for example, the "arm angle", the "couch height", the "FOV", and the "SID", as illustrated in FIG. 32. For example, once manipulation on a subject is started, the marker coordinate detection unit 26a executes the Learning mode, and stores a result of the Learning mode into the image data storage unit 25 or the like in association with the current conditions of manipulation. Here, a "result of the Learning mode" stored by the marker coordinate detection unit 26a is, for example, coordinate points indicating a region that includes positions at which a stent marker may be located. In one illustrative example, the marker coordinate detection unit 26a stores coordinate points of the four corners of the region R1 illustrated in FIG. 5 as a "result of the Learning mode". The marker coordinate detection unit 26a uses the stored information for the Learning mode to perform processing for detecting a stent marker in subsequent X-ray images. The corrected-image generation unit 26b then sets, as reference coordinate points, coordinate points of stent markers already detected by the marker coordinate detection unit 26a. The corrected-image generation unit 26b then generates corrected images by applying image displacement processing such as translational displacement or rotational displacement, or image deformation such as affine transform, to new images so that the coordinate points of the stent markers that have been detected by the marker coordinate detection unit 26a in new images can be the coordinate points of the reference coordinate points.

Here, the marker coordinate detection unit 26a executes the Learning mode each time there is a change in the conditions of manipulation, such as "arm angle", "couch height", "FOV", and "SID", and stores the changed conditions into the image data storage unit 25 or the like in association with a result of the Learning mode. More specifically, in stent implantation in a coronary artery, once the angle of the C-arm 15 is changed, the marker coordinate detection unit 26a executes the Learning mode again after the change, and stores a result of the Learning mode into the image data storage unit 25 or the like in association with the changed conditions. In this storing, the marker coordinate detection unit 26a stores a result of the Learning mode in association with each set of the conditions of manipulation. More specifically, the marker coordinate detection unit 26a stores, in the image data storage unit 25 or the like, respective results of the Learning mode before and after the change in angle of the C-arm 15. In this manner, for example, when collection of X-ray images is repeatedly performed with a plurality of sets of the conditions, a result of the Learning mode corresponding to a specific set of the conditions can be read out and used, whereby a processing time can be reduced.

In a case where the Learning mode is kept executed in the background during manipulation as described in the second embodiment, the marker coordinate detection unit 26a updates only the "results of the Learning mode". For example, while X-ray images are being collected, the marker coordinate detection unit 26a updates only the "results of the Learning mode" in the information for the Learning mode illustrated in FIG. 32 with respect to a certain set of the conditions every several tens of frames. Note that, when the difference between an already-stored result of the Learning mode and a result of the Learning mode that has been newly performed is small, the "results of the Learning mode" in the information for the Learning mode may be left without update. For example, the marker coordinate detection unit 26a may update the "results of the Learning mode" in the information for the Learning mode on condition that the distance between an already-stored result (coordinate points) of the Learning mode and a result of the Learning mode that has been newly performed exceeds a predetermined threshold.

The above-described embodiment illustrates, as an example, a case where results automatically extracted through the Learning mode are stored in association with the contents. However, the embodiment is not limited to this case, and the designation may be made by an operator. For example, the operator may designate a region including likely positions of a stent marker via the input unit 22 while observing moving images, and coordinate information on the designated region may be stored in association with the conditions. In such a case, the marker coordinate detection unit 26a accepts coordinate information on the region designated via the input unit 22, and stores the accepted coordinate information into the image data storage unit 25 or the storage unit (not illustrated) in association with the current conditions of manipulation.

Additionally, "the function of displaying as moving images X-ray images in which a stent appears stationary" explained in the above-described embodiments may be applied to processing executed on a real-time basis at the same time as X-ray irradiation, and may be applied to processing executed on X-ray images generated in a time-series manner in the past.

Furthermore, as medical treatment that is performed with reference to X-ray images, endovascular intervention treatment is illustrated as a case where a stent is used as a medical treatment tool. The present embodiments are not limited to this case, and are applicable to medical treatment tools for use in various kinds of medical treatment that is performed with reference to X-ray images.

Techniques according to the embodiments are applicable to, for example, treatment with the use of any of the following treatment devices by using the device as a marker: an electrode of an electrophysiological catheter for arrhythmia treatment; a Rotablator drill for treating a hard stricture site that is difficult to expand with a balloon or a stent; a holed metal cylinder attached on a tip end of a catheter for directional coronary atherectomy; and a catheter with an ultrasonic-wave transmitting-receiving function for checking conditions inside a blood vessel of a stricture site. Examples of treatment devices include: an angioscope; a vascular ultrasound device; a vascular magnetic resonance imaging (NRI) device; an optical coherence tomography (OCT) device; a device for implanting stem cells in the regenerative medicine field; an artificial valve; and a vascular graft. Furthermore, techniques according to the present embodiments can be applied to various clinical practices such as: hybrid treatment involving both a surgical aspect and an internal medicine aspect; and guidance on needling for biopsy in a surgical treatment.

As described above, at least one of the embodiments allows for a reduced processing time for image display.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to
sequentially generate X-ray images based on X-rays emitted from an X-ray tube and transmitted through a subject,
execute, in response to an instruction to start correction processing, first processing of identifying a target contained in the generated X-ray images and of storing an identification result in a memory;
execute second processing of detecting the target contained in newly generated X-ray images based on the identification result stored in the memory; and
generate corrected images by a correction processing to substantially match, with a reference position, a position of the detected target in an X-ray image other than a reference X-ray image, the reference position being the position of the detected target in the reference X-ray image included in the newly generated X-ray images,
wherein
upon receiving an instruction to start the correction processing, the processing circuitry is further configured to determine whether or not to execute the first processing again in accordance with a set of the conditions of manipulation on the subject.

2. The X-ray diagnostic apparatus according to claim 1, wherein, while the X-ray images are being generated, the processing circuitry is configured to execute the first processing and the second processing in parallel, and, when generation of the corrected images has failed, execute the second processing based on the identification result that is newly obtained in the first processing.

3. The X-ray diagnostic apparatus according to claim 1, wherein the processing circuitry is further configured to execute first processing where a target contained in an X-ray image generated by fluoroscopy is identified, and second processing where the target contained in X-ray images generated by radiography is detected based on the identification result of the first processing.

4. The X-ray diagnostic apparatus according to claim 2, wherein the processing circuitry is further configured to execute first processing where a target contained in an X-ray image generated by fluoroscopy is identified, and second processing where the target contained in X-ray images generated by radiography is detected based on the identification result of the first processing.

5. The X-ray diagnostic apparatus according to claim 1, wherein the processing circuitry is further configured to display on a display, as moving images, corrected images sequentially generated in the correction processing.

6. The X-ray diagnostic apparatus according to claim 2, wherein the processing circuitry is further configured to display on a display, as moving images, corrected images sequentially generated in the correction processing.

7. The X-ray diagnostic apparatus according to claim 3, wherein the processing circuitry is further configured to display on a display, as moving images, corrected images sequentially generated in the correction processing.

8. The X-ray diagnostic apparatus according to claim 4, wherein the processing circuitry is further configured to display on a display, as moving images, corrected images sequentially generated in the correction processing.

9. The X-ray diagnostic apparatus according to claim 5, wherein the processing circuitry is further configured to display, on the display, at least one of: an execution state of the first processing; an execution state of the second processing; and a result in terms of success or failure of the second processing.

10. The X-ray diagnostic apparatus according to claim 6, wherein the processing circuitry is further configured to display, on the display, at least one of: an execution state of the first processing; an execution state of the second processing; and a result in terms of success or failure of the second processing.

11. The X-ray diagnostic apparatus according to claim 7, wherein the processing circuitry is further configured to display, on the display, at least one of: an execution state of the first processing; an execution state of the second processing; and a result in terms of success or failure of the second processing.

12. The X-ray diagnostic apparatus according to claim 8, wherein the processing circuitry is further configured to display, on the display, at least one of: an execution state of the first processing; an execution state of the second processing; and a result in terms of success or failure of the second processing.

13. The X-ray diagnostic apparatus according to claim 1, wherein the processing circuitry is configured to identify the target, associated with a medical device inserted into a body of the subject, by using sequentially generated X-ray images, and detect the target in newly generated X-ray images, based on an identification result.

14. The X-ray diagnostic apparatus according to claim 13, wherein, when there has been any change in the conditions of manipulation on the subject, the processing circuitry is configured to change the identification result in accordance with the change in the conditions of manipulation, and detect the target contained in newly generated X-ray images, based on the changed identification result.

15. The X-ray diagnostic apparatus according to claim 1, wherein
the memory is configured to store therein the identification results with respect to each set of the conditions of manipulation including an angle of an arm, a height of a couch, a field of view (FOV), a source image receptor distance (SID), and a radiography condition, and
the processing circuitry is further configured to execute the second processing by using an identification result each time at least one of the conditions of manipulation is changed, the identification result corresponding to the changed conditions of manipulation.

16. An X-ray diagnostic apparatus, comprising:
processing circuitry configured to
sequentially generate X-ray images based on X-rays emitted from an X-ray tube and transmitted through a subject,
execute first processing of identifying a target contained in the generated X-ray images,
execute second processing of detecting the target contained in newly generated X-ray images, based on an identification result of the first processing, and
generate corrected images by a correction processing to substantially match, with a reference position, a position of the detected target in an X-ray image other than a reference X-ray image, the reference position being the position of the detected target in the reference X-ray image included in the newly generated X-ray images, wherein
while the X-ray images are being generated, the processing circuitry is configured to execute the first processing and the second processing in parallel, and, when generation of the corrected images has failed, execute the second processing based on the identification result that is newly obtained in the first processing.

17. The X-ray diagnostic apparatus according to claim 16, wherein the processing circuitry is further configured to display on a display, as moving images, corrected images sequentially generated in the correction processing.

18. The X-ray diagnostic apparatus according to claim 17, wherein the processing circuitry is further configured to display, on the display, at least one of: an execution state of the first processing; an execution state of the second processing; and a result in terms of success or failure of the second processing.

19. The X-ray diagnostic apparatus according to claim 16, wherein the processing circuitry is further configured to identify the target, associated with a medical device inserted into a body of the subject, by using sequentially generated X-ray images, and detect the target in newly generated X-ray images, based on an identification result.

20. The X-ray diagnostic apparatus according to claim 19, wherein, when there has been any change in the conditions of manipulation on the subject, the processing circuitry is configured to change the identification result in accordance with the change in the conditions of manipulation, and detect the target contained in newly generated X-ray images, based on the changed identification result.

* * * * *